US008487001B2

(12) United States Patent  (10) Patent No.: US 8,487,001 B2
Gagnon et al.                (45) Date of Patent:     Jul. 16, 2013

(54) MEDIUM-CHAIN LENGTH FATTY ACIDS, GLYCERIDES AND ANALOGUES AS NEUTROPHIL SURVIVAL AND ACTIVATION FACTORS

(75) Inventors: Lyne Gagnon, Quebec (CA); Jean Barabe, Quebec (CA); Pierre Laurin, Quebec (CA); Christopher Penney, Quebec (CA); Boulos Zacharie, Quebec (CA)

(73) Assignee: ProMetic BioSciences Inc., Laval, Quebec (CA)

( * ) Notice: Subject to any disclaimer, the term of this patent is extended or adjusted under 35 U.S.C. 154(b) by 0 days.

(21) Appl. No.: 12/814,028

(22) Filed: Jun. 11, 2010

(65) Prior Publication Data
US 2010/0279959 A1    Nov. 4, 2010

Related U.S. Application Data

(63) Continuation of application No. 10/475,266, filed as application No. PCT/CA02/00535 on Apr. 18, 2002, now Pat. No. 7,745,488.

(60) Provisional application No. 60/284,458, filed on Apr. 18, 2001.

(51) Int. Cl.
  *A61K 31/7024*  (2006.01)
  *A61K 31/23*    (2006.01)
  *A61K 31/22*    (2006.01)
  *A61K 31/198*   (2006.01)
  *C07C 235/06*   (2006.01)
  *C07C 235/12*   (2006.01)
  *A61P 7/00*     (2006.01)

(52) U.S. Cl.
  USPC ............. 514/552; 514/547; 514/563; 554/63

(58) Field of Classification Search
  None
  See application file for complete search history.

(56) References Cited

U.S. PATENT DOCUMENTS

| | | | | |
|---|---|---|---|---|
| 4,703,062 | A | * | 10/1987 | Blackburn et al. ............ 514/552 |
| 4,871,768 | A | | 10/1989 | Bistrian et al. |
| 5,631,219 | A | * | 5/1997 | Rosenthal et al. ........... 424/85.2 |
| 5,733,884 | A | * | 3/1998 | Barbul et al. .................... 514/5.5 |
| 6,060,459 | A | * | 5/2000 | von Borstel et al. ............ 514/45 |
| 6,326,360 | B1 | | 12/2001 | Kanazawa et al. |
| 6,689,351 | B1 | * | 2/2004 | Pierce et al. ................. 424/85.1 |
| 2002/0039595 | A1 | | 4/2002 | Keller |
| 2003/0176500 | A1 | * | 9/2003 | Molly et al. ................... 514/547 |
| 2003/0211972 | A1 | | 11/2003 | Backstrom et al. |
| 2004/0052836 | A1 | | 3/2004 | Li et al. |
| 2004/0147599 | A1 | | 7/2004 | Gagnon et al. |
| 2006/0128800 | A1 | | 6/2006 | Penney et al. |
| 2008/0051324 | A1 | | 2/2008 | Penney et al. |

FOREIGN PATENT DOCUMENTS

| | | |
|---|---|---|
| JP | 8-208510 | 10/1995 |
| JP | 10-265380 | 10/1998 |
| WO | WO 89/02275 | 3/1989 |
| WO | WO 95/30413 | 11/1995 |
| WO | WO 99/26640 | 6/1999 |
| WO | WO 99/45934 | 9/1999 |
| WO | WO 01/95914 | 12/2001 |
| WO | WO 02/083120 | 10/2002 |
| WO | WO 02/083122 | 10/2002 |
| WO | WO 2004/069237 | 8/2004 |
| WO | WO 2005/012217 | 2/2005 |

OTHER PUBLICATIONS

Beau et al., "Comparison of Bone Marrow Toxicity of Medium-Chain and Long-Chain Triglyceride Emulsions: An In Vitro Study in Humans", *Journal of Parenteral and Enteral Nutrition*, Nov. 1997, vol. 21, No. 6, pp. 343-346.

Bach et al., "The Usefulness of Dietary Medium-Chain Triglycerides in Body Weight Control: Fact or Fancy?" *Journal of Lipid Research*, 1996, pp. 708-726, vol. 37.

Beau et al., "Comparison of bone marrow toxicity of medium-chain and long-chain triglyceride emulsions: An in vitro study in humans," *J. Parent. Ent. Nutri.*, 1997, pp. 343-346, vol. 21.

Beers et al., "Leukopenia and lymphocytopenia," *The Merck Manual of Diagnosis and Therapy*, 1999, pp. 931-933.

Demirer et al., "Comparison of the efficacy of medium chain triglycerides with long chain triglycerides in total parenteral nutrition in patients with hematologic malignancies undergoing peripheral blood stem cell transplantation," *Clinical Nutrition*, 2000, pp. 253-258, vol. 19.

Duffy, K., et al., "Hydrazinonaphthalene and Azonaphthalene Thrombopoietin Mimics Are Nonpeptidyl Promoters of Megakaryocytopoiesis," *J. Med. Chem.*, Sep. 13, 2001, pp. 3730-3745, vol. 44.

Duffy, K., et al., "Identification of a Pharmacophore for Thrombopoietic Activity of Small, Non-Peptidyl Molecules. 1. Discovery and Optimization of Salicylaldehyde Thiosemicarbazone Thrombopoietin Mimics," *J. Med. Chem.*, Jul. 19, 2002, pp. 3573-3575, vol. 45 (with Supporting Information attached).

Hisha et al., "Isolation and identification of hematopoietic stem cell-stimulating substances from kampo (Japanese herbal) medicine, Juzen-taiho-to," *Blood*, 1997, pp. 1022-1030, vol. 90, No. 3.

(Continued)

*Primary Examiner* — James D Anderson
*Assistant Examiner* — Bong-Sook Baek
(74) *Attorney, Agent, or Firm* — France LeClaire

(57) ABSTRACT

A composition and method for promoting neutrophil survival and activation such as the treatment of neutropenia arising as an undesirable side effect of chemotherapy and radiation therapy. A composition containing medium-chain fatty acids, such as Capri acid or caprylic acid, or salts or triglycerides thereof, or mono- or diglycerides or other analogues thereof or medium-chain triglycerides (MCT) is administered to a human or animal needing treatment in an amount sufficient to reduce or eliminate neutropenia. The composition is administered in an amount effective to treat the disorder. The methods are also useful in the management of bone narrow transplantation and in the treatment of various neutropenic diseases.

20 Claims, 7 Drawing Sheets

OTHER PUBLICATIONS

International Search Report dated Mar. 3, 2003 for PCT/CA02/00535.

Ito, K., et al., "Maitake beta-glucan enhances granulopoiesis and mobilization of granulocytes by increasing G-CSF production and modulating CXCR4/SDF-1 expression," *Int Immunopharmacol.*, Jun. 30, 2009, pp. 1189-1196, vol. 9, No. 10.

Kusano, K., et al., "A potential therapeutic role for small nonpeptidyl compounds that mimic human granulocyte colony-stimulating factor," *Blood*, Sep. 25, 2003, pp. 836-842, vol. 103, No. 3.

Mizuno et al., "Effects of Salicylate and Other Enhancers on Rectal Absorption of Erythropoietin in Rats," *J. Pharm. Pharmacol.*, 1992, pp. 570-573, vol. 44.

Nijhof et al., "Isolation and Characterization of the Erythroid Progenitor Cell: CFU-E," *The Journal of Cell Biology*, Feb. 1983, pp. 386-392, vol. 96.

Office Action issued in U.S. Appl. No. 10/544,350, dated Feb. 7, 2008.

Office Action issued in U.S. Appl. No. 10/544,350, dated Aug. 26, 2008.

Office Action issued in U.S. Appl. No. 10/544,350, dated Mar. 2, 2009.

Office Action issued in U.S. Appl. No. 10/544,350, dated Nov. 24, 2009.

Santos et al., "Improvement of norfloxacin oral bioavailability by EDTA and sodium caprate," *International Journal of Pharmaceutics*, 2003, pp. 1-4, vol. 260.

Wang, Y., et al., "Role of the spleen in cyclophosphamide-induced hematosuppression and extramedullary hematopoiesis in mice," *Arch Med Res.*, Jun. 4, 2009, pp. 249-255, vol. 40, No. 4.

Kimoto et al., "Antitumor effect of medium-chain triglyceride and its influence on the self-defense system of the body," *Cancer Detection and Prevention*, 1998, pp. 219-224, vol. 22.

Pageau et al., "Systemic protection against radiation," *Radiat. Res.*, 1976, pp. 267-273, vol. 66.

Reya et al., "Abnormal myelocity cell development in interleukin-2 (IL-2)-deficient mice: Evidence for the involvement of IL-2 in myelopoiesis," *Blood*, 1998, pp. 2935-2947, vol. 91.

Wanten et al., "Phagocytosis and killing of *Candida albicans* by human neutrophils after exposure to structurally different lipid emulsions," *J. Parent. Ent. Nutrit.*, 2001, pp. 9-13, vol. 25.

Wanten et al., "Nutritional lipid emulsions modulate cellular signaling and activation of human neutrophils," *J. Lipid Res.*, 2001, pp. 428-436, vol. 42.

Wanten et al., "Saturated triglycerides and fatty acids activate neutrophils depending on carbon chain-length," *Eur. J. Clin. Invest.*, 2002, pp. 285-289, vol. 32.

Yamada et al., "Hematopoietic stem cell proliferation accelerator," data base Accession No. 124L97756 HCA, 1995.

\* cited by examiner

MEDIUM-CHAIN LENGTH FATTY ACIDS, GLYCERIDES AND ANALOGUES AS NEUTROPHIL SURVIVAL AND ACTIVATION FACTORS

CROSS-REFERENCE TO A RELATED APPLICATION

This application is a continuation application of application U.S. Ser. No. 10/475,266, filed Mar. 4, 2004 now U.S. Pat. No. 7,745,488; which is a National Stage Application of International Application Number PCT/CA02/00535, filed Apr. 18, 2002, which claims the benefit of U.S. Provisional Application Ser. No. 60/284,458, filed Apr. 18, 2001, which are incorporated herein by reference in their entirety.

FIELD OF THE INVENTION

The present invention relates to the prevention and/or treatment of neutropenia. This includes the treatment of neutropenia associated with the use of chemotherapy and radiotherapy as well as treatment of neutropenia arising from infections, hematologic diseases and nutritional deficiencies. The present invention also relates generally to reducing drug toxicity and enhancing drug efficacy. In particular, the present invention relates to the use of medium-chain length fatty acids such as capric acid, caprylic acid, or salts or triglycerides thereof or mono- or diglycerides or other analogues thereof as a neutrophil survival and activation factor or bone marrow stem cell proliferation factor.

BACKGROUND OF THE INVENTION

Chemotherapy refers to the use of cytotoxic agents such as, but not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin or chlorambucil in order to eradicate cancer cells and tumors. However, these agents are non-specific and, particularly at high doses, they are toxic to normal and rapidly dividing cells. This often leads to various side effects in patients undergoing chemotherapy and radiation therapy. Myelosuppression, a severe reduction of blood cell production in bone marrow, is one such side effect. It is characterized by leukopenia, neutropenia and thrombocytopenia. Severe chronic neutropenia (idiopathic, cyclic, and congenital) is also characterized by a selective decrease in the number of circulating neutrophils and an enhanced susceptibility to bacterial infections.

The essence of treating cancer with chemotherapeutic drugs is to combine a mechanism of cytotoxicity with a mechanism of selectivity for highly proliferating tumor cells over host cells. However, it is rare for chemotherapeutic drugs to have such selectivity. The cytotoxicity of chemotherapeutic agents limits administrable doses, affects treatment cycles and seriously jeopardizes the quality of life of the oncologic patient.

Although other normal tissues may also be adversely affected, bone marrow is particularly sensitive to proliferation-specific treatments such as chemotherapy or radiation therapy. Acute and chronic bone marrow toxicity is a common side effect of cancer therapies which leads to decreases in blood cell counts and anemia, leukopenia, neutropenia, agranulocytosis and thrombocytopenia. One cause of such effects is a decrease in the number of hematopoietic cells (e.g., pluripotent stem cells and other progenitor cells) caused by both a lethal effect of cytotoxic agents or radiation on these cells and by differentiation of stem cells provoked by a feedback mechanism induced by the depletion of more mature marrow compartments. The second cause is a reduction in self-renewal capacity of stem cells, which is also related to both direct (mutation) and indirect (agmg of stem cell population) effects. (Tubiana, M., et al., Radiotherapy and Oncology 29: 1-17, 1993). Thus, cancer treatments often result in a decrease in Polymorphonuclear Neutrophils (PMN) or neutropenia. PMN are the first line of defense against invading pathogens and play a central role during acute inflammation, their primary function being the phagocytosis and killing of the infectious agents. To accomplish this role, PMN leave the circulation in response to chemotactie factors and enter in the affected area to exert their biological functions. In individuals exhibiting normal blood cell counts, neutrophils constitute approximately 60% of the total leukocytes. (SI Units Conversion Guide, 66-67 (1992), New England Journal of Medicine Books). However, as many as one in three patients receiving chemotherapy treatment for cancer may suffer from neutropenia. Mean normal neutrophil counts for healthy human adults are on the order of 4400 cells/µL, with a range of 1800-7700 cells/µL. A count of 1,000 cells to 500 cells/µL is moderate neutropenia and a count of 500 cells/µL or less is severe neutropenia. Patients in myelosuppressive states are prone to infection and frequently suffer from blood-clotting disorders, requiring hospitalization. Lack of neutrophils and platelets is the leading cause of morbidity and mortality following cancer treatments and contributes to the high cost of cancer therapy. In these above-mentioned conditions, the use of any agent capable of inhibiting neutrophil apoptosis or stimulating neutrophil activation and mobilization can be of therapeutic value. Efforts to restore the patient's immune system after chemotherapy involves the use of hematopoietic growth factors to stimulate remaining stem cells to proliferate and differentiate into mature infection fighting cells.

In bone marrow transplantation, a phenomenon known as "mobilization" has also been exploited to harvest greater numbers of stem/progenitor cells from peripheral blood. This method is currently used for autologous or allogeneic bone marrow transplantation. Growth factors are used to increase the number of peripheral progenitor stem cells to be harvested before myeloablative therapy and infusion of progenitor stem cells.

Post-therapy bone marrow transplantation can also counter neutropenia. However, these treatments require 10-15 days of treatment which leaves patients vulnerable to infection. Agents capable of stimulating bone marrow stem cells can facilitate and accelerate stem cells engraftment thus shortening the neutropenic window following bone marrow transplantation.

Although hematopoietic growth factors such as granulocyte-macrophage colony stimulating factor (GM-CSF) and granulocyte colony stimulating factor (G-CSF) can exert such actions, their use is expensive since they have to be produced by recombinant technology. Such post-therapeutic ameliorative treatments are unnecessary if patients are "chemoprotected" from immune suppression.

Therefore, there is a need for novel compositions and methods to reduce the undesirable side effects of myelosuppressive states induced by chemotherapy and radiation therapy.

SUMMARY OF THE INVENTION

The present invention satisfies the need for chemoprotective agents by providing a novel method for the stimulation of the hematopoietic system in a mammal, including a human.

The present invention also provides a novel method for treating the myelosuppressive effects of chemotherapy and radiotherapy, and any other situation in which the stimulation of the hematopoietic system can be of therapeutic value such as, but not limited to, bone marrow transplantation and chronic neutropenia, as well as neutropenia resulting from infections, hematologic diseases and nutritional deficiencies. This method assists the hematopoietic system in countering myelosuppression, increasing neutrophil survival and activation, in patients undergoing such treatment.

In accordance with this method, a composition containing one or more medium-chain length fatty acids such as capric acid, caprylic acid, or salts or triglycerides thereof or mono- or diglycerides or other analogues in a pharmaceutically acceptable carrier is administered to a mammal, particularly humans, in an amount effective to prevent or treat neutropenia such as for reducing the adverse effects of chemotherapy and radiation therapy and for treating neutropenia arising from infections, hematologic diseases and nutritional deficiencies.

Accordingly, it is an object of the present invention to provide compositions using capric acid, caprylic acid, lauric acid or metallic salts (sodium, potassium, calcium, magnesium) thereof, or triglycerides thereof, or mono- or diglycerides or other analogues thereof for the production of chemoprotective pharmaceutical compositions as a single agent or as a combination of two or more agents with and/or without other chemotherapeutic agents or such drugs which induce a state of myelosuppression.

Another object of the present invention relates to the use of capric acid, caprylic acid or sodium salts or triglycerides thereof or mono- or diglycerides thereof or related compounds as a hematopoiesis stimulating factor.

Furthermore, the present invention includes compositions containing capric acid, caprylic acid or sodium salts or triglycerides thereof or mono- or diglycerides or other analogues thereof and the use of such compounds for the treatment of myelo suppression and subsequent immunosuppression.

An object of the invention relates also to the use of capric acid, caprylic acid or sodium salts or triglycerides thereof or mono- or diglycerides or other analogues thereof for the treatment of patients with severe chronic neutropenia.

Yet another object of the present invention relates to the use of capric acid, caprylic acid or sodium salts or triglycerides thereof or mono- or diglycerides or other analogues thereof as a neutrophil survival and activation factor.

The present invention also relates to the use of capric acid, caprylic acid or sodium salts or triglycerides thereof or mono- or diglycerides or other analogues thereof in conditions where neutrophil mobilization can be of therapeutic value such as autologus or allogeneic bone marrow transplantation.

It is an object of the present invention to provide a method effective for providing chemoprotection of a mammal, including a human.

Another object of the present invention is to provide a method effective for increasing the effectiveness of chemotherapy and radiation therapy in a mammal, including a human.

Yet another object of the invention is to provide methods for using more usual dosages, or even increasing the dose of chemotherapeutic compositions necessary to achieve a better therapeutic benefit, while avoiding increased side-effects.

Another object of the present invention is to provide a method effective for reducing or eliminating chemotherapy-induced neutropenia in a mammal, including a human.

Still another object of the present invention is to provide a method for treating neutropenia arising from hematologic diseases such as chronic idiopathic neutropenias, cyclic neutropenia, lazy-leukocyte syndrome, Chédiak-Higashi syndrome leukemia and aplastic anemia.

Yet another object of the present invention is to provide a method for treating neutropenia arising from infections such as viral (for example, HIV, measles, hepatitis, yellow fever, mononucleosis) and bacterial (for example, typhoid, paratyphoid, brucellosis) infections.

Finally, another object of the present invention is to provide a method that causes minimal or no adverse side effects in the recipient.

These and other objects, features and advantages of the present invention will become apparent after a review of the following detailed description of the disclosed embodiment and the appended claims.

DETAILED DESCRIPTION OF THE INVENTION

Figure 1:
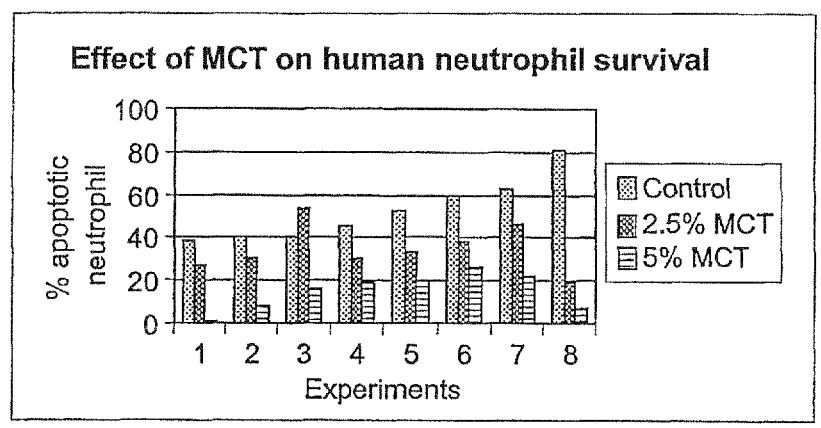
FIG. 1 shows the effect of MCT on PMN apoptosis.

High-dose chemotherapy and radiation destroy hematopoietic cells in bone marrow, leaving the patients severely depleted in neutrophils and platelets. After such treatments, patients spend several weeks in intensive care units due to infections and fever resulting from neutropenia. Thrombocytopenia leads to prolonged clotting time and bleeding disorders requiring platelet transfusions. Myelosuppression is a dose-limiting factor in cancer treatment and lack of neutrophils and platelets is the leading cause of morbidity and mortality following these cancer treatments.

In bone marrow transplantation, two approaches may be used. Before transplantation, stimulation of the bone marrow may increase the number of peripheral progenitor stem cells. However, freshly transplanted bone marrow does not contain sufficient mature neutrophils or neutrophil intermediaries to restore a patient's immune system. This leaves the patient with a period of increased susceptibility to infections and prolonged clotting time. Therapy involving neutrophil stimulation and activation increases recovery following bone marrow transplantation, by reducing neutropenia and thrombocytopenia.

The present invention relates to a method of promoting neutrophil survival and activation in a subject. Current methods are directed towards restoring the subject's hematopoietic system. Hematopoietic growth factors presently used for such treatment are granulocyte colony-stimulating factor (G-CSF), stem cell factor (SCF) and granulocyte-macrophage colony-stimulting factor (GM-CSF). G-CSF and GM-CSF can shorten the total period of neutropenia and thrombocytopenia but there still remains a significant window during which the patient is deficient in blood clotting and susceptible to infections.

In bone marrow transplantation, "mobilization" has also been used to harvest higher numbers of stem/progenitor cells from peripheral blood. Hematopoietic stem cells in the bone marrow are mobilized in the blood following treatment with growth factors. Growth factors used for such treatment include interleukin-3 (IL-3), G-CSF, GM-CSF, SCF and a recombinant fusion protein having the active moieties of both IL-3 and GM-CSF. Mobilized stem cells are then harvested after growth factor treatment and reinfused into the patient following the next round of high dose chemotherapy or irradiation, to restore the patient's neutrophils and platelets.

Medium-chain triglycerides (also referred to herein as "MCT") consist of glycerol esterified with fatty acids with carbon chain lengths of 8 (C8, octanoic acid or caprylic acid) and 10 (C10, decanoic acid or capric acid). MCT usually contain of a mixture of glycerol esters of C8 and C10 fatty acids. However, MCT can also contain small amounts (2±1% each) of glycerol esters of C6 (hexanoic acid or caproic acid) and C12 (dodecanoic acid or lauric acid). CRODAMOL™ is a commercially available MCT available from Croda Ltd., Toronto (Canada). As shown in example 1, CRODAMOL™ is an MCT which contains glycerol triesters of C8 and C10 fatty acids present in varying proportions. However, CRODAMOL™ does not contain any C6 or C12 fatty acid esters. Long-chain triglycerides (also referred to herein as "LCT"), on the other hand, consist of glycerol esterified with fatty acids with carbon chain lengths of greater than 12. Typical fatty acids present in LCT include palmitic (C16) and stearic (C18) acids. Unlike MCT, LCT is the primary component of dietary fats. Indeed, MCT and LCT have significantly different biological properties. Some of the physiological differences between MCT and LCT are described in Harrison's Principles of Internal Medicine, $8^{th}$ Edition, 1520-1521 (1977), McGraw Hill Book Company or $15^{th}$ Edition, 1668-1669 (2001). For example, MCT, in contrast to LCT, do not require hydrolysis by pancreatic lipase, since they can be absorbed by the intestinal epithelial cell.

MCT and their constituent medium-chain fatty acids are nontoxic materials which find use in the food and pharmaceutical industries. For example, K. A. Trani et al. in Food and Chemical Toxicology 38: 79-98 (2000) state that MCT have been utilized in an increasing number of food and nutrition applications because they offer a number of advantages over LCT. MCT are also used primarily as emulsifiers in various human and veterinary pharmaceutical preparations and in cosmetics. They refer to a number of toxicological studies which support the safety of MCT. For example, they note that the safety of human dietary consumption of MCT, up to levels of 1 g/kg, has been confirmed in clinical trials. C8 and C10 fatty acids possess similar safety and use. For example, in The Merck Index, $11^{th}$ Edition, 266 (1989) caprylic acid is reported to have an $LD_{50}$ (oral, rats)=10.08 g/kg which is essentially nontoxic. In fact, according to section 184 of the Code of Federal Regulations (CFR), the U.S. Federal Drug Agency (FDA) has granted caprylic acid a GRAS (Generally Recognized As Safe) affirmation. Similarly, according to section 172 (CFR) free fatty acids (e.g. capric, caprylic) and their metallic salts are recognized as safe additives for use in food. As noted by D. Dimitrijevic et al. in Journal of Pharmacy and Pharmacology 53: 149-154 (2001), capric acid (sodium salt) is approved for human use in Japan and Sweden as an absorption enhancer for rectal drug products. U.S. Pat. No. 4,602,040 (1986) describes the use of MCT as a pharmaceutical excipient. More recently, PCT publication WO 01/97799 describes the use of medium-chain fatty acids, in particular caprylic and capric acids, as antimicrobial agents.

However, until the unexpected findings disclosed herein, the effectiveness of medium-chain fatty acids such as capric acid, caprylic acid or metallic salts or mono-, di- or triglycerides (MCT) thereof as a neutrophil survival and activation factor was not known. As described herein, MCT contain triglycerides of C8 (caprylic) and C10 (capric) fatty acids which constitute at least 98% of the activity pertaining to stimulation of hematopoiesis and maturation of neutrophils. D. Waitzberg et al. in Nutrition 13: 128-132 (1997) state that lipid emulsions (LCT and MCT) only moderately decreases neutrophil bactericidal function and have no effect on monocytes. Indeed, the only publication which gives a vague indication that MCT may influence neutropenia describes clinical studies in which MCT are administered along with LCT and compared with LCT alone. No studies were undertaken with MCT alone and so the effect on immune function is not apparent. However, the results reported by S. Demirer et al. in Clinical Nutrition 19: 253-258 (2000) teaches that MCT exacerbate neutropenia when MCT are combined with LCT and relative to LCT alone. That is, it was suggested that MCT inhibit neutrophil function and/or survival. Somewhat supporting this suggestion, PCT publication WO 95/30413 asserts that unsaturated long chain fatty acids such as linolineic acid, as well as saturated long chain (C16 or longer) fatty acids, can function to enhance hematopoietic stem cell proliferation.

The present invention relates to the use of medium-chain fatty acids or metallic salts or triglycerides thereof or mono- or diglycerides or other analogues thereof or MCT as a hematopoiesis activation or growth factor and a neutrophil survival and activation factor. When used in chemotherapy and radiotherapy, a composition containing medium-chain fatty acids or metallic salts or triglycerides thereof or mono- or diglycerides or other analogues thereof or MCT is administered before, during and/or after the treatment in order to shorten the neutropenic window and to accelerate the replenishment of the hematopoietic system. Furthermore, it is possible to use a combination of medium-chain fatty acids along with their metallic salts or triglycerides thereof or mono- or diglycerides or other analogues thereof and/or MCT at multiple points relative to treatment with chemotherapy and radiotherapy (e.g., fatty acids before treatment and MCT after). Alternatively, it is possible to administer the combination simultaneously: before, during and/or after treatment with chemotherapy and radiotherapy. In severe neutropenia, a composition containing medium-chain fatty acids or metallic salts or triglycerides thereof or mono- or diglycerides or other analogues thereof or MCT is used as the therapeutic agent. In bone marrow transplantation, medium-chain fatty acids or metallic salts or triglycerides thereof or mono- or diglycerides or other analogues thereof or MCT is used to increase the number of peripheral stem cells available for transplantation after ablative radiotherapy or chemotherapy. Medium-chain fatty acids or metallic salts or triglycerides thereof or mono- or diglycerides or other analogues thereof or MCT can also be used after bone marrow transplantation in order to stimulate bone marrow stem cells thus shortening the time period for recovery from neutropenia.

The method is therefore useful for stimulating hematopoiesis to treat myelosuppression arising from chemotherapy or radiotherapy; chronic or transient neutropenia neutropenia; drug-induced neutropenia; and neutropenia arising from a hematologic disease, nutritional deficiency, infection, or radiotherapy. Transient neutropenia may arise from stress due to shipping of an animal or travel of a human or animal. The method is also useful for stimulating hematopoiesis to heal a wound in the patient, and to induce neutrophil mobilization to facilitate bone marrow transplantation in a patient.

As used herein, the terms "a" or "an" can mean one or more, depending on the context in which it is used.

As used herein, "medium-chain fatty acids such as capric acid or caprylic acid or metallic salts or triglycerides thereof or mono- or diglycerides or other analogues thereof or MCT composition" refers to a composition comprising said active ingredient and one or more pharmaceutically acceptable carriers.

As used herein, the term "pharmaceutically acceptable carrier" refers to a substance that does not interfere with the physiological effects of medium-chain fatty acids such as capric acid or caprylic acid or metallic salts or triglycerides thereof or mono- or diglycerides or other analogues thereof or MCT and that is not toxic to mammals including humans.

The capric or caprylic acid or salts or triglycerides thereof or mono- or diglycerides or other analogues thereof or MCT compositions of the present invention are formulated using capric or caprylic acid or salts or triglycerides thereof or mono- or diglycerides or other analogues thereof or MCT and pharmaceutically acceptable carriers by methods known to those skilled in the art (MERCK INDEX, Merck & Co., Rahway, N.J.). These compositions include, but are not limited to, liquids, oils, emulsions, aerosols, inhalants, capsules, pills, patches and suppositories.

All methods include the step of bringing the active ingredient(s) into association with the carrier which constitutes one or more accessory ingredients.

As used herein, the term "chemotherapy" refers to a process of killing proliferating cells using a cytotoxic agent. The phrase "during the chemotherapy" refers to the period in which the effect of the administered cytotoxic agent lasts. On the other hand, the phrase "after the chemotherapy" is meant to cover all situations in which a composition is administered after the administration of a cytotoxic agent regardless of any prior administration of the same and also regardless of the persistence of the effect of the administered cytotoxic agent.

When the method of this invention is applied to chemotherapy, a capric or caprylic acid or salts or triglycerides thereof or mono- or diglycerides or other analogues thereof or MCT composition can be administered prior to, during, or subsequent to the chemotherapy (i.e., prior to, during, or subsequent to the administration of a cytotoxic agent).

By "cytotoxic agent" is meant an agent which kills highly proliferating cells, e.g., tumor cells, virally infected cells, or hemopoietic cells. Examples of a cytotoxic agent which can be used to practice the invention include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin or chlorambucil, and an agonist of any of the above compounds. A cytotoxic agent can also be an antiviral agent, e.g., AZT (i.e., 3'-azido-3'-deoxythymidine) or 3TC/lamivudine (i.e., 3-thiacytidine).

As used herein, the term "leukopenia" refers to an abnormal reduction in the number of leukocytes in the blood.

As used herein, the term "neutropenia" refers to the presence of abnormally small numbers of neutrophils in the blood.

In one preferred embodiment, the pharmaceutical composition is in the form of any suitable composition for oral, sublingual administration or inhalation (nasal spray), intravenous, intramuscular, subcutaneous, for use in the treatment of neutropenia, thrombocytopenia or as a neutrophil survival and activation factor.

It will be appreciated that the amount of a composition of the invention required for use in the treatment will vary with the route of administration, the nature of the condition being treated, the age and condition of the patient, and will be ultimately at the discretion of the attendant physician. The desired dose may conveniently be presented in a single dose or as divided doses taken at appropriate intervals, for example as two, three, four or more doses per day.

While it is possible that, for use in therapy, medium-chain fatty acids or metallic salts or triglycerides thereof or mono- or diglycerides or other analogues thereof or MCT may be administered as the raw chemical, it is preferable to present the active ingredient as a pharmaceutical formulation.

In a preferred embodiment of this invention, the amount of active ingredient administered is such that the concentration in the blood (free and/or bound to serum albumin) is greater than 1 μM. In a particularly preferred embodiment, the concentration in the blood is greater than 1 mM.

In another embodiment, the pharmaceutical composition is in the form of oral (including sublingual), or parental (including intramuscular, subcutaneous rectal and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation. When desired, the above-described formulations adapted to give sustained release of the active ingredient may be employed.

Medium-chain fatty acids or salts or triglycerides thereof or mono-diglycerides or other analogues thereof or MCT can also be used in combination with other therapeutically active agents such as cytotoxic anticancer agents or other anticancer agents (immune modulating or regulating drugs or therapeutic vaccines or antiangiogenesis drugs, etc.), immune suppressive drugs (including anti-inflammatory drugs), a growth factor such as a colony stimulating factor (preferably GM-CSF or G-CSF), a cytokine such as interleukin 2 or interleukin 15, or combinations thereof. The individual components of such combinations may be administered either sequentially (before or after) or simultaneously in separate or combined pharmaceutical formulations. The combination referred to above may conveniently be presented for use in the form of a pharmaceutical formulation and thus pharmaceutical formulations comprising a combination as defined above together with a pharmaceutically acceptable carrier thereof comprise a further aspect of the invention.

In a preferred embodiment of the method of stimulting hematopoiesis in a patient needing treatment, a pharmacologically effective amount of a composition containing one or more of the following compounds, or combinations thereof, are administered:

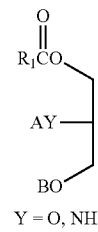

Y = O, NH

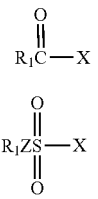

Z = O, NH, CH$_2$O
= zero wherein
R$_1$ is a straight chained or branched, saturated or unsaturated C7-C11 alkyl group;
A and B are hydrogen or $$R_1-\overset{O}{\underset{\|}{C}},$$

independently; and
X is a hydroxyl group, an oxy anion with a metallic mono- or dicationic counterion, or an alkoxy group with a straight chained or branched C1-C4 alkyl moiety.

It will be understood by those skilled in the art that, in formula III, the term "Z=zero" indicates that the variable Z is optional and may be eliminated or replaced with a hydrogen.

In an alternative preferred embodiment, the composition contains a mixture of at least two compounds described by formula I, which are Medium Chain Triglycerides (MCTs) wherein A, B and R$_1$ are the same and are straight chained or branched, saturated or unsaturated C7 and C9 alkyl groups, respectively. Alternatively, the composition contains a mixture of two triglycerides wherein a first MCT is described by formula I, wherein A, B and R$_1$ are CH$_3$(CH$_2$)$_6$, and a second MCT is described by formula I, wherein A, B and R$_1$ are CH$_3$(CH$_2$)$_8$. Alternatively, the composition further contains from 0.1% to 3% each of a third compound described by formula I, wherein A, B and R$_1$ are CH$_3$(CH$_2$)$_4$, and a fourth compound described by formula I, wherein A, B and R$_1$ are CH$_3$(CH$_2$)$_{10}$. Alternatively, the composition is a mixture containing four geometric isomers of C8 and C10 fatty acid triglycerides described by the following formula:

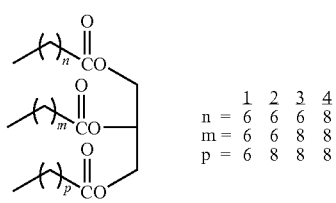

|   | 1 | 2 | 3 | 4 |
|---|---|---|---|---|
| n = | 6 | 6 | 6 | 8 |
| m = | 6 | 6 | 8 | 8 |
| p = | 6 | 8 | 8 | 8 |

In an alternative preferred embodiment, the composition contains one or more compounds described by formula II or formula III, wherein X is OH or X is an oxy anion with a metallic counterion such as calcium, magnesium, potassium, and sodium.

In a more preferred embodiment, the composition is caprylic acid, capric acid, sodium caprylate, sodium caprate, calcium caprylate, calcium caprate, caprylic acid triglyceride, or capric acid triglyceride.

The compositions and methods described herein include the following analogues and compounds:

aza analogues of caprylic acid triglyceride or capric acid triglyceride, preferably where the aza analogue is 1,2,3-O,N,O-trioctanoyl serinol or 1,2,3-O,N,O-tridecanoyl serinol;

the compound described by formula IV

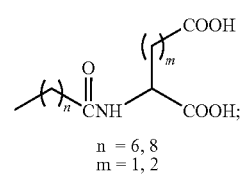

n = 6, 8
m = 1, 2 the compound described by formula V

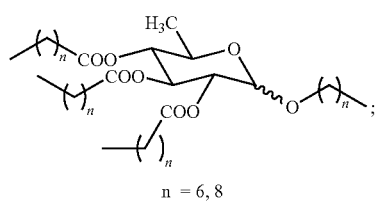

n = 6, 8 the compound described by formula VI, which provide a pharmaceutical formulation by degradation in vivo to release active substances described above

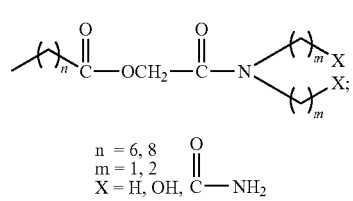

n = 6, 8
m = 1, 2
X = H, OH, $\overset{O}{\underset{\|}{C}}-NH_2$

The following examples further illustrate the practice of this invention, but are not intended to be limiting thereof. It will be appreciated that the selection of the dose of medium-chain fatty acids or salts or triglycerides thereof or mono- or diglycerides or other analogues thereof or MCT and related pharmaceutical formulations to be administered to any individual patient (human or animal) will fall within the discretion of the attending physician, will be prescribed in a manner commensurate with the appropriate dosages and will depend on the stage of the disease and like factors uniquely within the purview of the attending physician.

Example 1

Analysis of CRODAMOL™ (MCT: Caprylic/Capric Triglyceride)

CRODAMOL™ GTCC lot #T1033-1299 from Croda Ltd. (Toronto, Canada) was analyzed by gas chromatography. GC FID-analysis, conditions of the gradient: 100° C.-250° C. in 10 minutes, then 250° C. for 25 minutes; FID 250° C. Four peaks were observed: 22.04 minutes (26%), 25.07 minutes (43%), 29.16 minutes (25%) and 34.75 minutes (5%).

A sample of caprylic triglyceride (tricaprylin), obtained from Sigma-Aldrich lot #079H1212, was analyzed by gas chromatography. GC FID-analysis, conditions of the gradient: 100° C.-250° C. in 10 minutes, then 250° C. for 25 minutes; FID 250° C. Mainly one peak at 22.31 minutes (98%).

Example 2

Acylation of Alcohol Using Acid Chloride and Pyridine Base

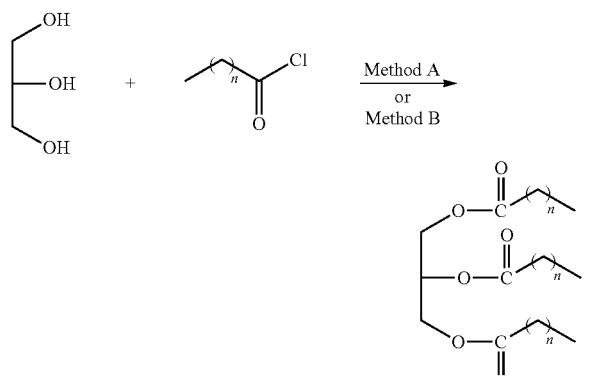

n = 6-10
Method A: Pyridine, $CH_2Cl_2$
Method B: DMAP, $CH_2Cl_2$

General Method A (Pyridine)

A solution of the alcohol (~0.1 M) in dry $CH_2Cl_2$ and pyridine (4:1), was cooled to 0° C. under nitrogen, and treated with the acid chloride (1.2 equivalent). The reaction was allowed to warm slowly to ambient temperature, and stirred overnight. TLC analysis ($SiO_2$, EtOAc 1:9 hexane) showed no remaining alcohol. The reaction mixture was diluted with $CH_2Cl_2$, and washed with saturated aqueous $NH_4Cl$ solution. The aqueous phase was extracted with $CH_2Cl_2$ (×1) and hexane (×1), and combined organic phases were washed with saturated aqueous NaCl solution, dried over $Na_2SO_4$, filtered and evaporated in vacuo to give the crude product.

General Method B (DMAP)

A solution of the alcohol (~0.1 M) in dry $CH_2Cl_2$ was cooled to 0° C. under nitrogen, and treated with DMAP (1.3 equivalent) and the acid chloride (1.2 equivalent). The reaction was allowed to warm slowly to ambient temperature, and was stirred overnight. TLC analysis ($SiO_2$, EtOAc 1:9 hexane) showed no remaining alcohol. The reaction mixture was diluted with $CH_2Cl_2$, and washed with saturated aqueous $NH_4Cl$ solution. The aqueous phase was extracted with $CH_2Cl_2$ (x1) and hexane (x1), and combined organic phases were washed with saturated aqueous NaCl solution, dried over $Na_2SO_4$, filtered and evaporated in vacuo to give the crude product.

Example 3

Nonanoic Acid Triglyceride

Glycerol (120 mg, 1.30 mmol) was acylated with nonanoyl chloride (751 μl, 4.16 mmol) according to General Method A, example 2. Purification by column chromatography (Isolute™ $SiO_2$, eluting with 0-5% EtOAc in hexane) gave two product containing fractions, which were evaporated in vacuo to give the desired product as a colourless liquid, in 89% (127 mg, 19%) and 93% (475 mg, 71%) purity respectively (GC/FID). $R_f$ 0.46 ($SiO_2$, 10% ethyl acetate in hexane); $^1H$ NMR ($CDCl_3$, 300 MHz) $\delta_H$=5.27 (m, 1H), 4.29 (dd, 2H), 4.14 (dd, 2H), 2.31 (m, 6H), 1.61 (m, 6H), 1.27 (m, 30H), 0.88 (t, 9H); MS ($FAB^+$) m/z=510($M-H^+$); GC FID-analysis, conditions: gradient 100° C.-250° C. in 10 minutes, then 250° C. for 25 minutes; FID 250° C.; 27.25 minutes.

Example 4

Nonanoic acid Diglyceride and Monoglyceride

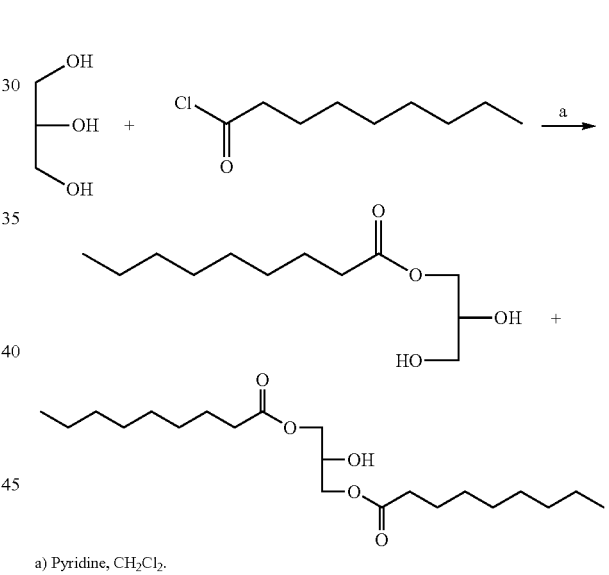

a) Pyridine, $CH_2Cl_2$.

Glycerol (100 mg, 1.09 mmol) was acylated with one equivalent of nonanoyl chloride (205 μl, 1.09 mmol) according to General Method A, example 2. Purification by Biotage™ (40S, $SiO_2$, eluting with 10% ethyl acetate in hexane-100% ethyl acetate) gave a colorless oil. Two different compounds were obtained:

Nonanoic acid Diglyceride was obtained (73 mg, 18%) as a white solid. mp 24-26° C.; $R_f$ 0.52 ($SiO_2$ pretreated with $Et_3N$, 30% ethyl acetate in hexane); $^1H$ NMR ($CDCl_3$, 300 MHz) $\delta_H$=4.17 (m, 5H), 2.35 (t, 4H), 1.63 (m, 4H), 1.27 (m, 20H), 0.88 (t, 6H); MS ($FAB^+$) m/z=373 ($M+H^+$).

Nonanoic acid Monoglyceride was obtained (85 mg, 34%) as a white solid. mp 37-38.5° C.; $R_f$ 0.08 ($SiO_2$ pretreated with $Et_3N$, 30% ethyl acetate in hexane); $^1H$ NMR ($CDCl_3$, 300 MHz) $\delta_H$=4.18 (m, 2H), 3.94 (m, 1H), 3.69 (m, 1H), 3.62 (m, 1H), 2.36 (t, 2H), 1.62 (m, 2H), 1.28 (m, 10H), 0.88 (t, 3H); MS ($FAB^+$) m/z=233 ($M+H^+$).

Example 5

1,2,3-O,N,O-Tridecanoyl serinol

Serinol (51 mg, 0.56 mmol) was acylated with decanoyl chloride (372 µl, 1.76 mmol) according to General Method B, example 2. Purification by MPLC (SiO$_2$, eluting with 0 then 10% EtOAc in hexane) gave the desired product as a white solid (301 mg, 97%). mp 54° C.; TLC, R$_f$ 0.85 (SiO$_2$, EtOAc 2:3 hexane); $^1$H NMR (CDCl$_3$, 300 MHz) δ$_H$ 0.84 (9H, t), 1.20-1.27 (36H, m), 1.52-1.60 (6H, m), 2.13 (2H, t), 2.28 (4H, t), 4.03 (2H, 2×A of 2×ABX), 4.19 (2H, 2×B of 2×ABX,), 4.41-4.46 (1H, m), 5.70 (1H, d); HRMS m/e calcd for C$_{33}$H$_{63}$NO$_5$ 553.4706 Found 553.4713. GC-FID analysis, conditions of the gradient: 100° C.-250° C. in 10 minutes, then 250° C. for 25 minutes; FID 250° C. Mainly one peak at 14.80 minutes (98%).

Example 6

1,3-O,O-Didecanoyl serinol

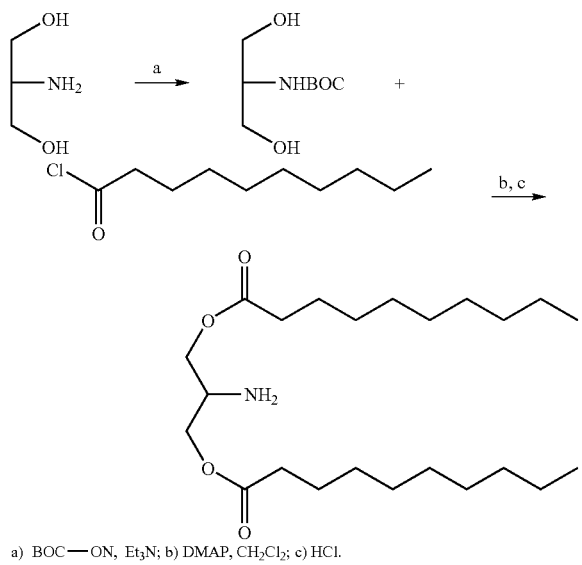

a) BOC—ON, Et$_3$N; b) DMAP, CH$_2$Cl$_2$; c) HCl.

A solution of serinol (1.57 gm, 17.2 mmol) in acetone (17 ml) and water (17 ml), was treated with triethylamine (3.60 ml, 25.9 mmol) and BOC—ON (4.67 gm, 19.0 mmol), and the reaction was stirred under nitrogen overnight. Acetone was evaporated in vacuo, and the crude mixture was partitioned between EtOAc and water. The aqueous phase was extracted with EtOAc (×3), and combined organic extracts were dried over Na$_2$SO$_4$, filtered and evaporated in vacuo, to give a yellow solid. Purification by HPLC (SiO$_2$, eluting with 40 to 80% EtOAc in hexane) gave the N—BOC-diol intermediate as a white crystalline solid (2.10 gm, 64%). TLC, R$_f$ 0.15 (SiO$_2$, EtOAc 4:1 hexane); $^1$H NMR (CDCl$_3$, 300 MHz) δ$_H$ 1.40 (9H, s), 3.54-3.56 (5H, m).

The N—BOC-diol intermediate (50 mg, 0.26 mmol) was acylated with decanoyl chloride (173 µl, 0.83 mmol) according to General Method B. Purification by MPLC (SiO$_2$, eluting with 0 then 10% EtOAc in hexane) gave the N—BOC-diacyl intermediate as a colourless oil (115 mg, 88%). TLC, R$_f$ 0.80 (SiO$_2$, EtOAc 2:3 hexane); $^1$H NMR (CDCl$_3$, 300 MHz) δ$_H$ 0.87 (6H, t), 1.23-1.30 (24H, m), 1.44 (9H, s), 1.56-1.70 (4H, m), 2.31 (4H, t), 4.04-4.21 (4H, m), 4.77-4.80 (1H, m), 6.73 (1H, d).

A solution of the N—BOC-diacyl intermediate (76 mg, 0.15 mmol) in dry CH$_2$Cl$_2$ (1.5 ml) was cooled to 0° C., and treated with a solution of 4.0 M anhydrous HCl in 1,4-dioxane (375 µl, 1.50 mmol; final concentration 0.8 M). The reaction was allowed to warm to room temperature, and stirred for 3 hr at the same temperature. A further portion of 4.0 M anhydrous HCl in 1,4-dioxane (375 µl, 1.50 mmol) was added, and the reaction was stirred for a further 2 hr. Evaporation of solvents gave the desired product, as a white solid (69 mg, 100%). mp 101° C.; TLC, R$_f$ 0.40 (SiO$_2$, EtOAc 2:3 hexane); $^1$H NMR (CDCl$_3$, 300 MHz) δH 0.88 (6H, t), 1.20-1.29 (24H, m), 1.55-1.65 (4H, m), 2.45-2.52 (4H, m), 3.72-3.80 (1H, m), 4.30-4.51 (2H, m), 8.6-9.0 (3H, br m); HRMS m/e calcd for (M−HCl), C$_{23}$H$_{45}$NO$_4$ 339.3348 Found 339.3340; GC-FID analysis, conditions of the to gradient: 100° C.-250° C. in 10 minutes, then 250° C. for 25 minutes; FID 250° C. Mainly one peak at 17.14 minutes (94%).

Example 7

α- and β-O-Methyl-2,3,4,—O,O,O-tridecanoyl-L-fucopyranose

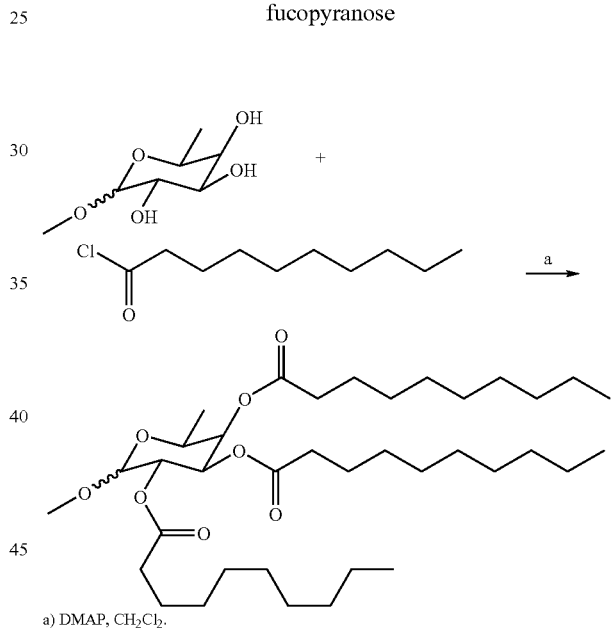

a) DMAP, CH$_2$Cl$_2$.

1-O-Methyl-L-fucopyranose (593 mg, 3.33 mmol) was synthesised according to the method of Levene & Muskat (J. Biol. Chem. 105:431-441, 1934) and was acylated with decanoyl chloride (2.90 ml, 14.0 mmol) according to General Method B, example 2. Purification by MPLC (SiO$_2$, eluting with 0 to 5% EtOAc in hexane) gave the α (1.18 gm, 55%) and β (0.52 gm, 24%) of the desired product as a colourless oil.

Data for α anomer: TLC, R$_f$ 0.45 (SiO$_2$, EtOAc 1:9 hexane); $^1$H NMR (CDCl$_3$, 300 MHz) δ$_H$ 0.87 (9H, t), 1.14 (3H, d), 1.20-1.35 (36H, m), 1.52-1.68 (4H, m), 2.18 (2H, t), 2.29 (1H, A of ABX$_2$), 2.32 (1H, B of ABX$_2$), 2.41 (2H, t), 3.38 (3H, s), 4.13 (1H, qd, J 6.5), 4.93 (1H, d), 5.15 (1H, dd, 5.30 (1H, dd), 5.36 (1H, dd); FIRMS m/e calcd for (M-CH$_3$O) C$_{36}$H$_{65}$O$_7$ 609.4730 Found 609.4720.

Data for β anomer: TLC, R$_f$ 0.40 (SiO$_2$, EtOAc 1:9 hexane); $^1$H NMR (CDCl$_3$, 300 MHz) δ$_H$ 0.87 (9H, t, J=6.5 Hz), 1.22 (3H, d), 1.20-1.35 (36H, m), 1.49-1.67 (4H, m), 2.18 (2H, t), 2.25 (1H, A of ABX$_2$), 2.29 (1H, B of ABX$_2$), 2.34

(2H, t), 3.50 (3H, s), 3.81 (1H, qd), 4.35 (1H, d), 5.03 (1H, dd), 5.19 (1H, dd), 5.24 (1H, dd).

Example 8

L-Glutamate Capramide

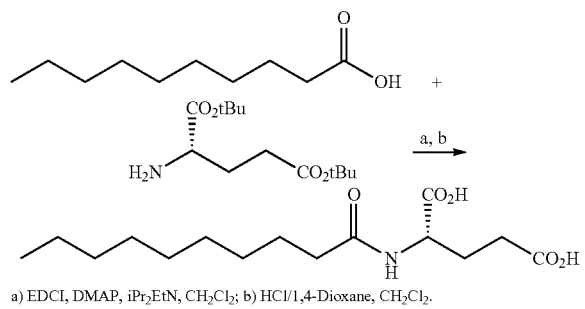

a) EDCI, DMAP, iPr₂EtN, CH₂Cl₂; b) HCl/1,4-Dioxane, CH₂Cl₂.

To a solution of capric acid (7.30 mmol, 1.26 g) in dry $CH_2Cl_2$ (60 ml) was added under nitrogen L-glutamic acid di-t-butyl ester HCl salt (6.09 mmol, 1.80 gm), DMAP (1.8 mmol, 0.22 g), diisopropylethylamine (18 mmol, 3 ml) and 1-(3-dimethylaminopropyl)-3-ethylcarbodiimide HCl salt (EDCI) (7.30 mmol, 1.40 gm). The resulting colorless solution was stirred at room temperature for 24 hr. The solvent was then removed under reduced pressure to give a white oily residue. Purification by Biotage™ (40S $SiO_2$, eluting with 5% ethyl acetate in hexane-30% ethyl acetate in hexane) gave a colorless oil, which was L-glutamate di-t-butylester capramide (2.47 gm, 98%). $R_f$ 0.56 ($SiO_2$, 30% ethylacetate in hexane); $^1H$ NMR ($CDCl_3$, 300 MHz) $\delta_H$=6.05 (d, 1H), 4.45 (m, 1H), 2.30 (m, 2H), 2.27 (m, 2H), 2.16 (t, 2H), 2.07 (m, 1H), 1.87 (m, 1H), 1.58 (m, 2H), 1.43 (s, 9H), 1.41 (s, 9H), 1.23 (m, 12H), 0.84 (t, 3H).

Deprotection of the BOC group was achieved by a slow addition of a solution 4.0 M HCl in 1,4-dioxane (23 ml) to a solution of the di-t-butyl ester derivative (5.75 mmol, 2.38 gm) in $CH_2Cl_2$ (35 ml) at 0° C. The colorless solution was allowed to warm to room temperature and stirred for an additional 20 hr. The solvent was then removed under reduced pressure and the resulting white solid was dried to yield L-glutamate capramide (1.71 gm, 99%). mp 95-96.5° C.; $^1H$ NMR ($CD_3OD$, 300 MHz) $\delta_H$=4.39 (m, 1H), 3.27 (d, 1H), 2.36 (t, 2H), 2.20 (t, 2H), 2.13 (m, 1H), 1.90 (m, 1H), 1.58 (m, 2H), 1.27 (m 12H), 0.86 (t, 3H); MS (ES⁺) m/z=324 (M+Na⁺), 302 (M+H⁺); MS (ES) m/z=300 (M−H⁺); HPLC analysis, conditions: gradient 0.01% TFA in 10%-70% acetonitrile in 10 minutes; flow 1.0 ml/min; 210 nm; 8.93 minutes.

Example 9

Capric Acid N,N-dimethylacetamide ester

To a solution of capric acid (8.7 mmol, 1.5 g) in anhydrous DMF (80 ml) under nitrogen was added sodium iodide (0.87 mmol, 130 mg) followed by dimethylchloroacetamide (9.6 mmol, 985 μl). Potassium carbonate (9.6 mmol, 1.3 g) was then added and the resulting suspension stirred at 90° C. for 5 days. The reaction was allowed to cool at room temperature, and then was mixed with distilled water. The product was extracted with ethyl acetate (x3). The combined organic phases were washed with aqueous solution of $NaHCO_3$, dried with $Na_2SO_4$, filtered, and concentrated under reduced pressure. The yellow liquid obtained was purified by Biotage™ (40M, $SiO_2$, eluting with 25% ethyl acetate in hexane-50% ethyl acetate in hexane). Capric acid N,N-dimethylacetamide ester was obtained (2.03 gm, 92%) as a white powder. mp 42-42.5° C.; $R_f$ 0.55 ($SiO_2$, ethyl acetate); $^1H$ NMR ($CDCl_3$, 300 MHz) $\delta_H$=4.64 (s, 2H), 2.92 (s, 3H), 2.91 (s, 3H), 2.38 (t, 2H), 1.62 (qt, 2H), 1.22 (m, 12H), 0.83 (t, 3H); MS (ES⁺) m/z=537 (2M+Na⁺), 280 (M+Na⁺), 258 (M+H⁺).

Example 10

In Vitro Assays of Neutrophil Apoptosis and Survival

Neutrophil survival was measured as described by Lagraoui and Gagnon (Cell. Mol. Biol. 43:313-318, 1997). Neutrophils were obtained from the peripheral blood of healthy volunteers. Blood was submitted to gradient centrifugation with Lympholyte-poly (Cedarlane, Hornby, Canada) followed by hypotonic lysis of contaminating erythrocytes. Cells were suspended in RPMI (Gibco, Burlington, Canada) supplemented with 10% FBS (Hyclone, Logan USA). Final cell preparations consisted of >95% neutrophils as determined by Wright Giemsa staining. Viability was greater than 97% as determined by trypan blue exclusion. Polymorphonuclear leukocytes (PMN) have a short half-life and rapidly undergo characteristic changes indicative of apoptosis. Apoptosis was assessed according to the method described by Nicoletti et al., J. Immunol. Meth. 139:271-279 (1991). Briefly, freshly isolated neutrophils were incubated for 24 hr at 37° C. with different concentrations of MCT. After incubation, cells were stained with propidium iodide (PI, Sigma) and analyzed for apoptosis using an XL Flow Cytometer (Coulter). Data were then expressed as the percent of apoptotic cells. FIG. 1 represents a compilation of several experiments in which neutrophil apoptosis was measured in the absence (control) or the presence of various concentrations of MCT. The results indicate that in the presence of MCT in vitro, neutrophil apoptosis is inhibited by up to 90% and that the inhibition is dose-dependent. Thus, MCT can increase neutrophil survival and can be used as a neutrophil survival factor.

Example 11

In Vitro Assays of PMN Phagocytosis

Neutrophils (2×10⁶/ml) were incubated for 24 hr, at 37° C. in 5% $CO_2$ and 95% humidity with various concentrations of MCT. After 24 hr, viability was determined by trypan blue exclusion and cells were washed three times with PBS containing 2 mM glucose, 1 mM $MgCl_2$ and 1 mM $CaCl_2$. The cell concentration was then adjusted to 1×10⁶ cells/nil and then incubated with fluoresbrite carboxylate microspheres (1/10 dilution). After 30 minutes of incubation, neutrophils were washed and fixed in 2% paraformaldehyde. Fixed neutrophils were analyzed for microspheres ingestion using XL Flow Cytometer (Coulter). Data were then expressed as the percent of phagocytic cells.

Figure 2:
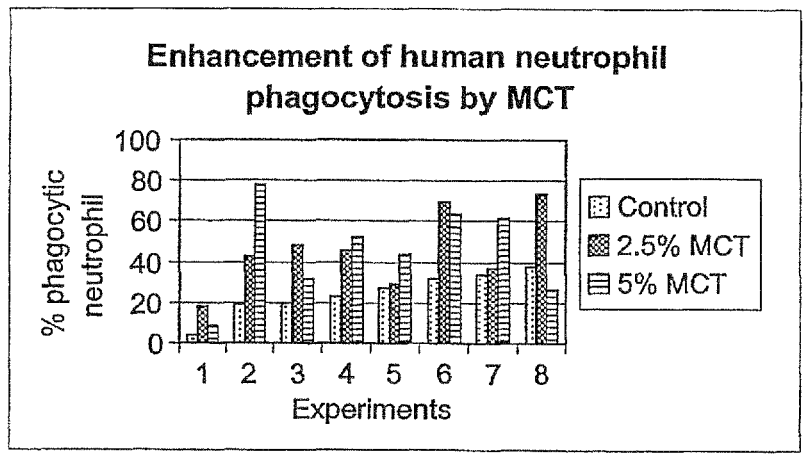
FIG. 2 shows the effect of MCT on PMN phagocytosis.

FIG. 2 represents a compilation of several experiments which measure PMN phagocytic activity in the absence (control) or the presence of various concentrations of MCT. The results indicate that MCT enhances the phagocytic activity of human PMN. The phagocytic activity is enhanced up to two to three times from the control values and the extent of the stimulation depends on the immune status of the donor.

Example 12

Effect of Doxorubicin on Neutrophil Apoptosis

Figure 3A:
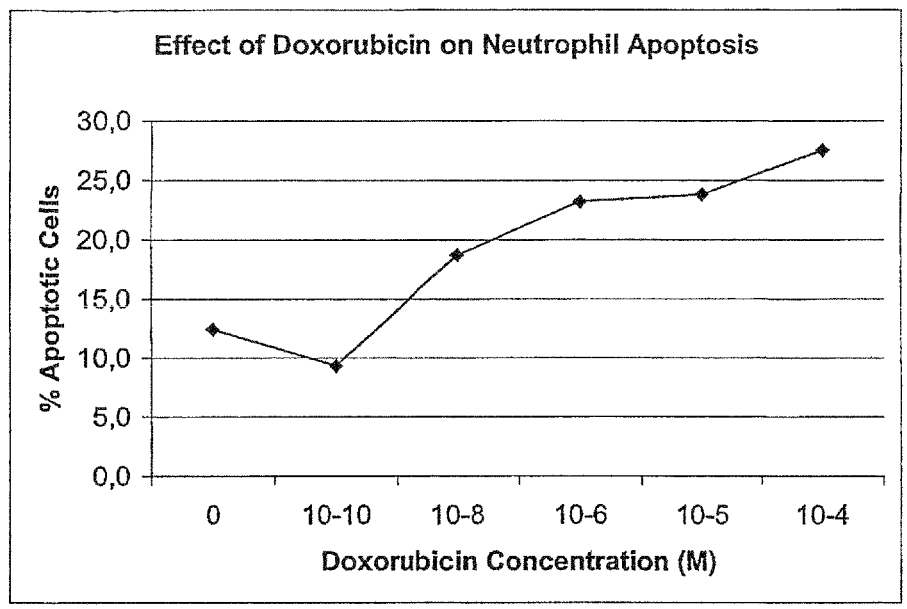
FIGS. 3A and 3B show the effect of doxorubicin on PMN apoptosis.
Figure 3B:
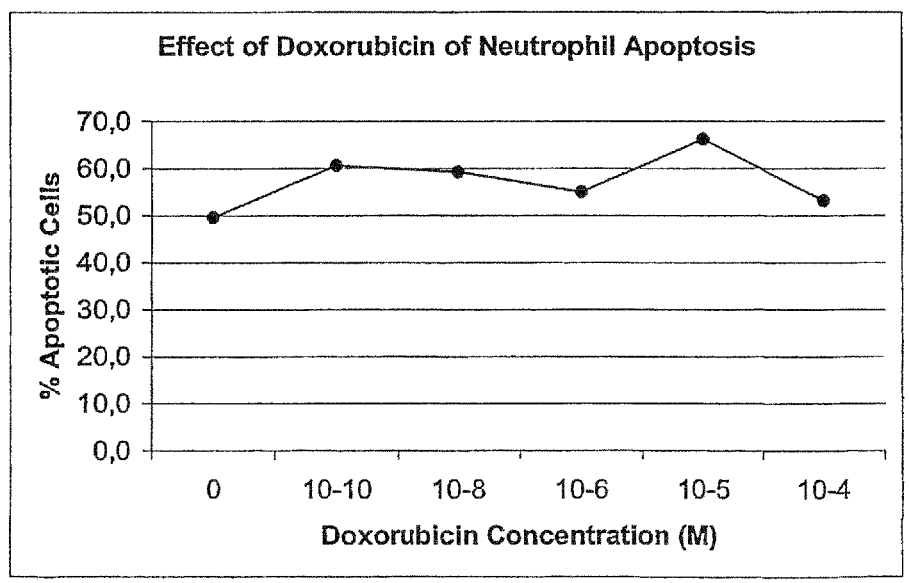

PMN were isolated as described in example 10. Cells ($2 \times 10^6$/ml) were incubated for 4 hr, at 37° C. in 5% $CO_2$ and 95% humidity in the presence of various concentrations of a chemotherapeutic agent, doxorubicin. Apoptotic cells were evaluated as described in example 10. Data are expressed in percent of apoptotic cells. FIGS. 3A and 3B indicate that doxorubicin induces PMN apoptosis.

Example 13

MCT Rescues the Doxorubicin-Induced Apoptosis of Neutrophils

PMN were isolated as described in example 10. Cells ($2 \times 10^6$/ml) were incubated for 4 hr, at 37° C. in 5% $CO_2$ and 95% humidity in the presence of various concentrations of doxorubicin with or without MCT (2.5% and 5.0%). Apoptotic cells were evaluated as described in example 10. Data are expressed in percent of apoptotic cells.

Figure 4A:
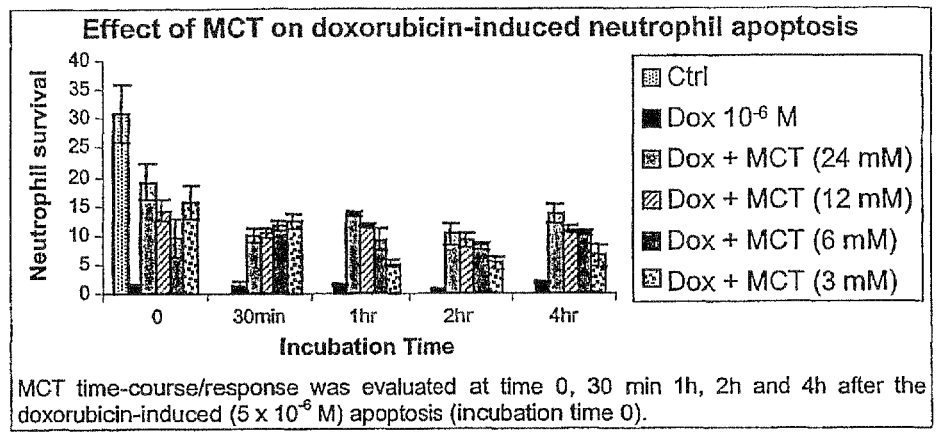
FIG. 4A represents a time-course response of MCT on doxombicin-treated neutrophils.

Table 1 represents two experiments measuring the chemoprotective effects of MCT on PMN. Results are expressed in percent of apoptotic cells after 4 hr of incubation in the presence or the absence of doxorubicin with or without MCT. As in example 12, doxorubicin induces PMN apoptosis in vitro. However, in the presence of MCT, at a concentration of 2.5% and 5% (v/v), the apoptotic effects of doxorubicin are inhibited. Thus, MCT exerts an anti-apoptotic action on PMN. Apoptosis was also studied using the annexin V-FITC/PI (propidium iodide) to method according to the manufacturer's Biosources recommendations (Apotarget Annexin-VFITC Apoptosis Kit #PHN 1018). Annexin V binds to phosphatidylserine which is transferred from the internal to external membrane in early to late phase apoptosis. Briefly, neutrophils are incubated in the presence or absence of varying concentrations of doxorubicin and MCT. After 24 hr, neutrophils are washed with PBS and stained with 2 µA of Annexin V-FITC and 10 µl of PI (Sigma, 1 mg/ml) for 20 minutes. After incubation, stained cells were fixed in paraformaldehyde (1%) and analyzed for apoptosis using an XL Flow Cytometer (Coulter). Data were then expressed as the percent of apoptotic cells. FIG. 4A represents a time-course response of MCT on doxorubicin-treated neutrophils. MCT rescues human neutrophil doxorubicin-induced apoptosis in a time- and dose-dependent manner.

Figure 4B:
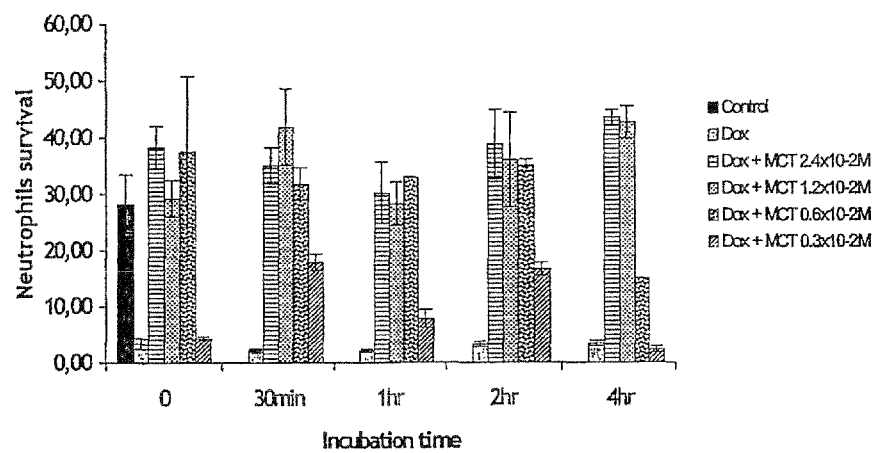
FIG. 4B represents a time-course response of doxorubicin on MCT-treated neutrophils.

FIG. 4B represents a time-course response of doxorubicin on MCT-treated neutrophils. MCT protects, in a dose-dependent manner, neutrophils against doxorubicin-induced apoptosis up to 4 hr before the introduction of the toxic agent (doxorubicin).

TABLE 1

Protective effect of MCT on doxorubicin-induced neutrophil apoptosis

| | % Apoptosis of neutrophils (PMN) | | | | | |
|---|---|---|---|---|---|---|
| | Experiment 1 | | | Experiment 2 | | |
| Doxorubicin Concentration | Control | MCT 2.5% (v/v) | MCT 5% (v/v) | Control | MCT 2.5% (v/v) | MCT 5% (v/v) |
| 0 | 12.4 | 9.5 | 12.3 | 49.6 | 23.6 | 4.6 |
| $10^{-10}$ M | 9.3 | 11.7 | 7.4 | 60.6 | 14.7 | 23.9 |
| $10^{-8}$ M | 18.7 | 14.2 | 8.3 | 59.2 | 32.5 | 14.8 |
| $10^{-6}$ M | 23.2 | 12.7 | 3.5 | 55.0 | 21.6 | 16.9 |
| $10^{-5}$ M | 23.8 | 12.3 | 8.3 | 66.2 | 74.7 | 12.1 |
| $10^{-4}$ M | 27.5 | 35.2 | 17.1 | 53.2 | 58.6 | 55.7 |

Example 14

MCT Rescues the Doxorubicin-Induced Apoptosis of Neutrophils Comparison to GM-CSF Table 2 represents the effect of GM-CSF, MCT and tricaprylin on doxorubicin-induced human neutrophil apoptosis. GM-CSF and MCT are able to rescue or protect human neutrophils against doxorubicin-induced apoptosis. Tricaprylin rescues doxorubin-induced apoptosis and further enhances the viability of human neutrophils to a higher extent than that observed in the non-treated neutrophils (control, absence of doxorubicin).

TABLE 2

Protective effect of MCT and GM-CSF on doxorubicin-induced neutrophil apoptosis

| | % PMN Viability |
|---|---|
| Control | 35.9 ± 0.71 |
| Doxorubicin (DOX) ($10^{-5}$ M) | 6.82 ± 0.5 |
| GM-CSF ($10^{-7}$ M) + DOX | 16.75 ± 2.05 |
| GM-CSF ($10^{-8}$ M) + DOX | 6.99 ± 0.23 |
| MCT (24 mM) + DOX | 14.20 ± 1.98 |
| MCT (12 mM) + DOX | 12.37 ± 1.72 |
| Tricaprylin (24 mM) + DOX | 12.13 ± 1.25 |
| Tricaprylin (12 mM) + DOX | 42.95 ± 6.15 |

Example 15

MCT and Tricaprin Increase In Vitro Murine Bone Marrow Proliferation

Bone marrow cells were obtained from the femur of female C57BL/6 mice (6- to 8-weeks old). Cells were flushed and washed with PBS. Collected cells are centrifuged and resuspended at $2 \times 10^6$ cells/ml. 100 µl of cells ($2 \times 10^5$ cells) are incubated in a 96-well microliter plate for 48 hr in the presence or absence of MCT or tricaprin. After incubation, cells are pulsed with 1 µCi of [$^3$H]-thymidine for 6 hr. Plates are harvested on a Tomteck and counted on a Microbeta β-counter. Incorporation of [$^3$H]-thymidine in the DNA is a direct indication of the to cell proliferation.

Figure 5:
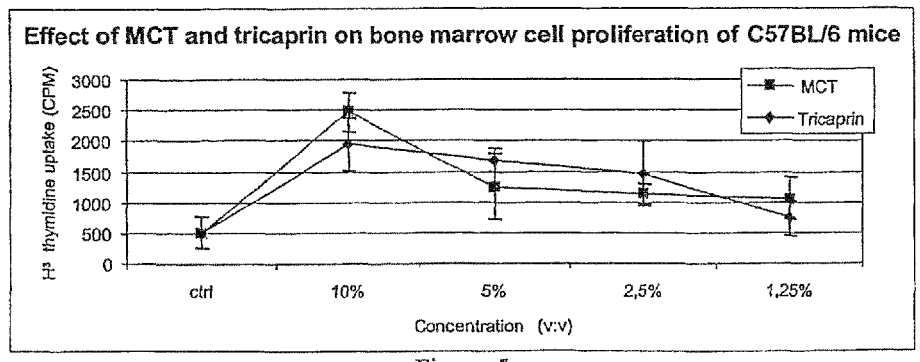
FIG. 5 shows the effect of MCT and tricaprin on bone marrow proliferation.

FIG. 5 represents a typical experiment on the effect of MCT and tricaprin on bone marrow proliferation. MCT and tricaprin increase bone marrow proliferation by 3- to 5-fold relative to the control.

Example 16

Chemoprotection Studies: In Vivo Induction of Immune Cells Proliferation or Protection by MCT Female C57BL/6 mice, 6 to 8 week old, were immunosuppressed by treatment with 80 mg 5-fluorouracil (5-FU) or 100-200 mg of cyclophosphamide (CY) or 12 mg of taxotere (TX) administered intravenously at day 0. To examine the immunoprotective effect of MCT or other compounds, mice were pre-treated orally at day-3, -2 and -1 or treated intravenously at day 0 with the test compound. Mice were sacrificed at day +5 by cardiac puncture and cervical dislocation. Then, cell suspensions were prepared from thymus, spleen and bone marrow as follow.

Tissues were crushed in PBS buffer and contaminating erythrocytes were lysed in ACK buffer (155 mM $NH_4Cl$, 12 mM $NaHCO_3$, 0.1 mM EDTA, pH 7.3) for 5 minutes. Cells were then collected by centrifugation and washed three times in PBS and resuspended in tissue culture medium. Cells were counted on a hemacytometer.

Results show that MCT significantly increases the number of cells in immune tissues of normal and immunosuppressed animals compared to the vehicle alone as shown in the following tables and figures. Depending on the experiments and the immune status of the mice, MCT can increase the bone marrow cell and/or the spleen cell and/or the thymus cell counts.

Figure 6:
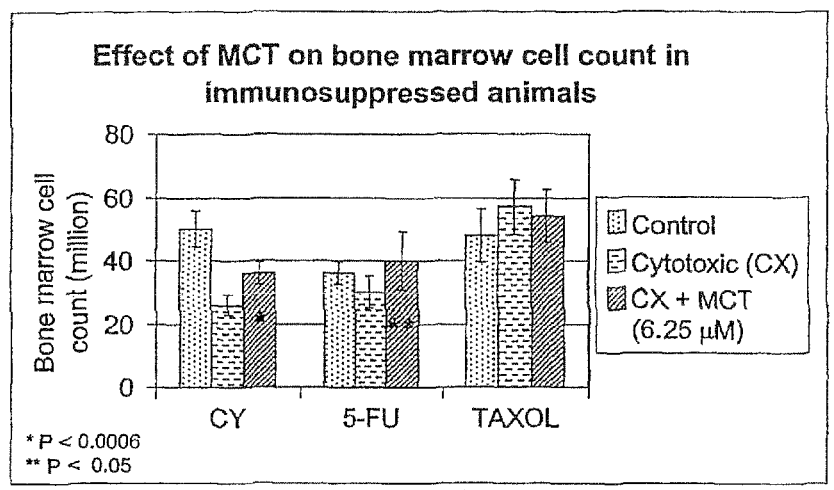
FIG. 6 shows the effect of MCT on bone marrow cell count in immunosuppressed animals.

FIG. 6 shows the effect of MCT on bone marrow cell count in immunosuppressed animals. Only CY and 5-FU depressed the bone marrow cell count compared to the control (no cytotoxic treatment). In mouse, taxotere treatment has no significant effect on bone marrow cell count. In suppressed bone marrow, administration of MCT (6.25 μMole per mouse) at day-3, -2 and -1 enhanced significantly the bone cell marrow count.

Figure 7:
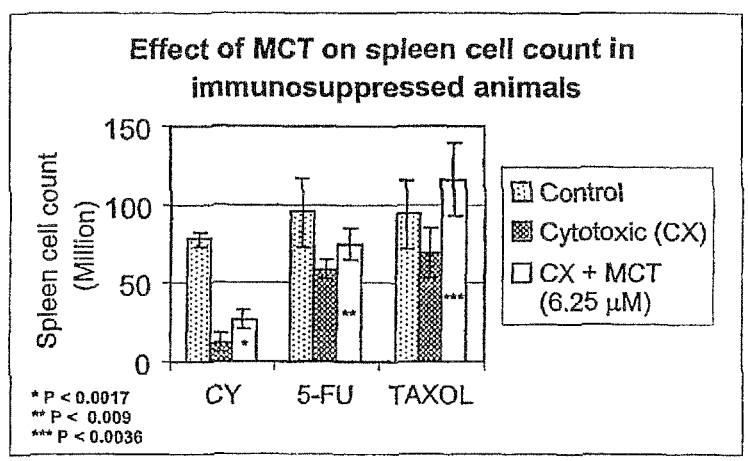
FIG. 7 shows the effect of MCT on spleen cell count in immunosuppressed animals.

FIG. 7 represents the effect of MCT on spleen cell count in immunosuppressed mice which received the pre-treatment regimen of MCT per o.s. All cytotoxic drugs (CY, 5-FU and TX) reduce significantly the spleen cell count compared to the control. Administration of MCT (6.25 μMole per mouse) at day -3, -2 and -1 significantly increases spleen cell count with "P" less than 0.0017, 0.009 and 0.0036 for CY, 5-FU and TX respectively.

Furthermore, MCT significantly enhances bone marrow cell count in normal mice when administered i.v. at day 0 (table 3). However, one i.v. injection of MCT is not sufficient to improve the spleen cell count in both normal and immunosuppressed mice.

TABLE 3

Effect of cyclophosphamide (CY) and CY + MCT on bone marrow and spleen cells (normal mice)

| | Bone Marrow | | Spleen | |
|---|---|---|---|---|
| | # Cells (×10$^6$) | P | # Cells (×10$^6$) | P |
| Control | 16 ± 3.94 | | 94 ± 11 | |
| CY | 13 ± 3.92 | 0.17 | 60 ± 12 | 0.0014 |
| CY + MCT (50 μMole) | 17 ± 4.28 | 0.87 | 53 ± 10 | 0.0003 |
| CY + MCT (12.5 μMole) | 17 ± 6.15 | 0.95 | 51 ± 10 | 0.0002 |
| MCT (50 μMole) | 41 ± 6.11 | >0.0001 | 103 ± 7 | 0.19 |
| MCT (12.5 μMole) | 27 ± 4.19 | 0.0018 | 101 ± 11 | 0.31 |

Example 17

Chemoprotection Studies: In Vivo Dose-Response of MCT Induction of Immune Cell Proliferation when Administered at Day-3, -2 and -1 In Normal Mice In vivo dose-response of MCT induction of immune cell proliferation in normal mice was assessed by the protocol described in example 16.

Table 4 represents the dose-response on treatment of MCT orally administered at day -3, -2 and -1 in normal mice. MCT significantly increases the bone marrow and spleen cell counts.

TABLE 4

Effect of MCT on normal mice

| | Bone Marrow | | Spleen | |
|---|---|---|---|---|
| | # Cells (×10$^6$) | P | # Cells (×10$^6$) | P |
| Control | 45 ± 7.3 | | 120 ± 12.9 | |
| MCT (3.15 μMole) | 52 ± 4.3 | 0.10 | 144 ± 15.8 | 0.018 |
| MCT (6.25 μMole) | 59 ± 11.3 | 0.05 | 134 ± 13.9 | 0.129 |
| MCT (12.5 μMole) | 54 ± 6 | 0.04 | 144 ± 19.8 | 0.04 |
| MCT (25 μMole) | 56 ± 3.9 | 0.01 | 127 ± 17.0 | 0.48 |

Example 18

Figure 8:
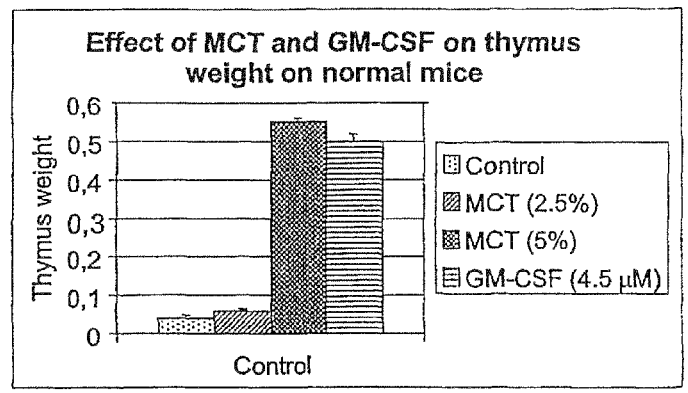
FIG. 8 shows the effect of MCT and GM-CSF on thymus weight on normal mice.

Chemoprotection studies: In Vivo Induction of Immune Cells Proliferation or Protection: Comparison of the Effect of MCT Versus Gm-CSF In vivo comparison on the induction of immune cell proliferation/regeneration or protection was undertaken following the protocol described in example 16. Comparative studies of MCT and GM-CSF were performed on normal and immunosuppressed animals. Compared to MCT, GM-CSF has no significant activity on bone marrow and spleen cell counts in immunosuppressed animals. A significant effect of GM-CSF was observed only on thymus weight in normal mice (FIG. 8). In this case, MCT displayed a similar effect to GM-CSF.

Example 19

Chemoprotection Studies

The effect of caprylic acid and capric acid on in vivo induction of immune cell proliferation or protection was assessed by the protocol described in example 16. As shown in table 5, only capric acid significantly enhances the bone marrow cell counts. No significant effect was demonstrated on spleen cell counts, compared to cyclophosphamide treated mice.

TABLE 5

Effect of cyclophosphamide (CY), CY + caprylic acid and CY + capric acid on bone marrow and spleen cells

| | Bone Marrow | | | Spleen | | |
|---|---|---|---|---|---|---|
| | # Cells (×10$^6$) | P/Control | P/CY | # Cells (×10$^6$) | P/Control | P/CY |
| Control | 54 ± 5.9 | >0.0001 | | 66 ± 7.3 | >0.0001 | |
| CY | 22 ± 5.7 | >0.0001 | | 23 ± 4.0 | >0.0001 | |
| CY + caprylic acid | 26 ± 3.58 | 0.001 | 0.21 | 28 ± 6.4 | >0.0001 | 0.17 |
| CY + capric acid | 32 ± 2.71 | 0.0004 | 0.006 | 27 ± 8.4 | >0.0001 | 0.27 |

Example 20

Chemoprotection Studies

The effect of tricaprylin and tricaprin on in vivo induction of immune cell proliferation or protection assessed by the protocol described in example 16. Tricaprylin and tricaprin are both efficacious in the proliferation or protection of bone marrow cell counts in CY-treated mice (table 6). No significant effect was observed on the spleen cell count, compared to cyclophosphamide treated mice.

TABLE 6

Effect of cyclophosphamide (CY), CY + tricaprylin and CY + tricaprin on bone marrow and spleen cells

| | Bone Marrow | | | Spleen | | |
|---|---|---|---|---|---|---|
| | # Cells ($\times 10^6$) | P/Control | P/CY | # Cells ($\times 10^6$) | P/Control | P/CY |
| Control | 55 ± 9.3 | | | 113 ± 15.9 | | |
| CY | 22 ± 5.8 | 0.0001 | | 36 ± 13.6 | >0.0001 | |
| CY + tricaprylin | 34 ± 7.8 | 0.0033 | 0.022 | 37 ± 12.6 | >0.0001 | 0.8 |
| CY + tricaprin | 31 ± 3.8 | 0.0008 | 0.012 | 38 ± 6.8 | >0.0001 | 0.7 |

Example 21

Chemoprotection Studies

The effect of nonanoic acid and lauric acid on in vivo induction of immune cell proliferation or protection assessed by the protocol described in example 16. Significant increases in proliferation or protection of bone marrow and spleen cell counts were observed with the pre-treatment of lauric acid in CY-treated mice. However, nonanoic acid demonstrates weak (not significant) activity on immune cell counts (table 7) compared to cyclophosphamide treated mice.

TABLE 7

Effect of cyclophosphamide (CY), CY + nonanoic acid and CY + lauric acid on bone marrow and spleen cells

| | Bone Marrow | | | Spleen | | |
|---|---|---|---|---|---|---|
| | # Cells ($\times 10^6$) | P/Control | P/CY | # Cells ($\times 10^6$) | P/Control | P/CY |
| Control | 58 ± 11.8 | | | 99 ± 22 | | |
| CY | 32 ± 6.3 | 0.0016 | 1.0 | 24 ± 6 | 0.0002 | |
| CY + nonanoic acid (6.25 μMole) | 36 ± 5.6 | 0.0044 | 0.26 | 28 ± 4 | 0.0004 | 0.27 |
| CY + lauric acid (6.25 μMole) | 42 ± 7.8 | 0.0185 | 0.04 | 32 ± 5 | 0.0005 | 0.03 |

Example 22

Chemoprotection Studies

The effect of trilaurin and trimyristin on in vivo induction of immune cell proliferation or protection assessed by the protocol described in example 16. Trilaurin and trimyristin have weak (not significant) activity on bone marrow and spleen cell counts on CY-immunosuppressed mice (table 8).

TABLE 8

Effect of cyclophosphamide (CY), CY + trilaurin and CY + trimyristin on bone marrow and spleen cells

| | Bone Marrow | | | Spleen | | |
|---|---|---|---|---|---|---|
| | # Cells ($\times 10^6$) | P/Control | P/CY | # Cells ($\times 10^6$) | P/Control | P/CY |
| Control | 49 ± 7.3 | | | 105 ± 23 | | |
| CY | 27 ± 2.8 | 0.0014 | | 19 ± 6.5 | 0.0007 | |
| CY + trilaurin (6.25 μM) | 31 ± 6.8 | 0.0028 | 0.219 | 28 ± 19.5 | 0.0004 | 0.302 |
| CY + trimyristin (6.25 μM) | 31 ± 9.9 | 0.0067 | 0.402 | 15 ± 4.6 | 0.0007 | 0.314 |

Example 23

Chemoprotection Studies

The effect of tricaproin and sodium caproate on in vivo induction of immune cell proliferation or protection assessed by the protocol described in example 16. Tricaproin and sodium caproate have a weak (not significant) activity on bone marrow and spleen cell counts on CY-immunosuppressed mice (table 9).

TABLE 9

Effect of cyclophosphamide (CY), CY + tricaproin and CY + sodium caproate on bone marrow and spleen cells

| | Bone Marrow | | | Spleen | | |
|---|---|---|---|---|---|---|
| | # Cells ($\times 10^6$) | P/Control | P/CY | # Cells ($\times 10^6$) | P/Control | P/CY |
| Control | 48 ± 4.9 | | | 98 ± 24.2 | | |
| CY | 25 ± 4.9 | >0.0001 | | 33 ± 13.2 | 0.0018 | |
| CY + tricaproin (6.25 μMole) | 29 ± 4.1 | 0.0001 | 0.17 | 37 ± 8.7 | 0.0035 | 0.51 |
| CY + sodium caproate (6.25 μMole) | 39 ± 17.9 | 0.2403 | 0.09 | 35 ± 10.6 | 0.0026 | 0.77 |

Example 24

Chemoprotection Studies

The effect of sodium caprylate and sodium caprate on in vivo induction of immune cell proliferation or protection assessed by the protocol described in example 16.

Figure 9:
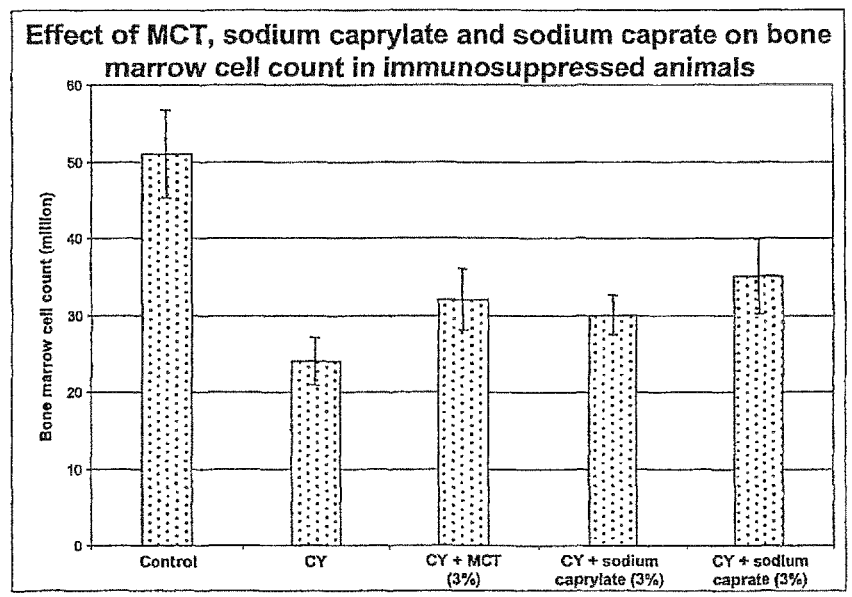
FIG. 9 shows the effect of MCT, sodium caprylate and sodium caprate on bone marrow cell count in immunosuppressed animals.

A significant increase in proliferation or protection of bone marrow cell count was observed with pre-treatment with sodium caprylate and sodium caprate in CY-treated mice (FIG. 9).

Example 25

Chemoprotection Studies: Post-Treatment Regimens

Chemoprotection studies were performed as described in example 16 except that mice were (post)-treated with MCT, sodium caprylate, sodium caprate or capric acid per o.s. on day 1, 2, 3 and 4.

A significant increase in bone marrow cell count was observed with the post-treatment of MCT, sodium caprylate and sodium caprate in CY-treated mice (table 10). When used as post-treatment, capric acid induces a significant increase in spleen cell count and a weak increase in bone marrow cell count (table 11).

TABLE 10

Effect of cyclophosphamlde (CY), CY + MCT, CY + sodium caprylate and CY + sodium caprate post-treatmeat on bone marrow and spleen cells

| | Bone Marrow | | | Spleen | | |
|---|---|---|---|---|---|---|
| | # Cells ($\times 10^6$) | P | P/CY | # Cells ($\times 10^6$) | P | P/CY |
| Control | 52 ± 6.17 | | | 110 ± 29.3 | | |
| CY | 19 ± 4.99 | >0.0001 | | 30 ± 9.5 | 0.0007 | |
| CY + MCT (12.5 μM) | 26 ± 3.70 | >0.0001 | 0.0189 | 38 ± 7.2 | 0.0014 | 0.163 |
| CY + sodium caprylate (12.5 μM) | 26 ± 5.33 | >0.0001 | 0.0455 | 36 ± 12.5 | 0.0009 | 0.394 |
| CY + sodium caprate (12.5 μM) | 29 ± 4.45 | 0.0001 | 0.0140 | 28 ± 6.3 | 0.0007 | 0.696 |

TABLE 11

Effect of cyclophosphamlde (CY), CY + capric acid post-treatment on bone marrow and spleen cells

| | Bone Marrow | | | Spleen | | |
|---|---|---|---|---|---|---|
| | # Cells ($\times 10^6$) | P/Control | P/CY | # Cells ($\times 10^6$) | P/Control | P/CY |
| Control | 48 ± 7.9 | | | 88 ± 15.9 | | |
| CY | 31 ± 6.7 | 0.0026 | | 21 ± 4.3 | 0.0001 | |
| CY + capric acid (3.125 μMole) | 37 ± 7.8 | 0.0326 | 0.209 | 31 ± 8.7 | 0.0001 | 0.035 |
| CY + capric acid (6.25 μMole) | 38 ± 4.6 | 0.0274 | 0.066 | 25 ± 6.3 | 0.0001 | 0.187 |
| CY + capric acid (12.5 μMole) | 38 ± 7.4 | 0.0412 | 0.134 | 36 ± 7.8 | 0.0002 | 0.003 |

Example 26

Chemoprotection Studies: Immunophenotyping Assay

Female, 6- to 8-week old, C57BL/6 mice were pre-treated on day -3, -2 and -1 per o.s. or intravenously at day 0 with different concentrations of MCT. Immunophenotyping was also performed on immunosuppressed animals. Immununo-suppression was achieved with 80 mg/kg of 5-fluorouracil (5-FU) or 100 to 200 mg/kg of cyclophosphamide (CY) or 12 mg/kg of taxotere (TX) injected i.v. on day 0. Mice were sacrificed on day 5 by cardiac puncture. Blood and spleens were collected and cell suspensions prepared and erythrocytes lysed in ACK buffer (155 mM $NH_4Cl$, 12 mM $NaHCO_3$, 0.1 mM EDTA, pH 7.3) for 5 minutes. The cells were washed three times in PBS, pH 7.4 and resuspended in tissue culture medium. The cells were then incubated for 45 minutes on ice with fluorescein isothiocyanate (FITC) or phycoerythrin (PE) conjugated cell surface marker according to the manufacturer's (Gibco/BRL, Cedarlane, Boehringer Mannheim) recommendation. The cells were then washed in PBS, fixed with 1% paraformaldehyde and analyzed with a Coulter XL flow cytometer. Analysis of the cell subsets was undertaken by determination of standard cell surface markers which were as follows: TCR (T-cell receptor), CD4 (T helper), CD8 (T cytotoxic/suppressor), CD11b (macrophage), NK (NK cells) and Ly5 (B-cells). Bone marrow cells were obtained as described in example 15. Cells were stained by a 45 minutes incubation of FITC or PE conjugated cell surface marker according to the manufacturer's recommendation. The cells were then washed in PBS, fixed with 1% paraformaldehyde and analyzed with a Coulter XL flow cytometer. Analysis of the cell subsets was undertaken by determination of standard cell surface markers which were as follows: CD34 (hematopoietic progenitor cells), CD41 (platelets, megakaryocytes), CD13 (myelomonocytic stem cells, myelocytes, promonocytes) and CD38 (lymphoid stem cells, pro-B, pre-B). Table 12 represents the effect of MCT on blood and spleen immunophenotyping in normal mice. On blood immunophenotyping, MCT increase CD8+ and LY5+ cell subsets. In some experiments, MCT increases weakly the LY5-TCR-subset (data not shown). On spleen immunophenotyping, MCT increases significantly the relative percentage of LY5+TCR+ and CD4+ cells. LY5-TCR- are non B-non T-cells that may represent the neutrophils.

When administered to immunosuppressed mice, MCT increases the relative percentage of LY5-TCR- (probably neutrophils) and CD11+ (macrophage) cells on blood and spleen immunophenotyping compared to cyclophosphamide alone. These cell subsets origmate from the myeloid cell precursor (table 13).

TABLE 12

Effect of MCT on blood and spleen immunophenotyping in normal mice

| Cell subsets | Control | 6.25 μM | 12.5 μM | 50 μM |
|---|---|---|---|---|
| | Blood Immunophenotyping | | | |
| CD8+ | 12.76 ± 1.23 | 16.41 ± 1.16 p ≤ 0.0004 | — | 13.18 ± 2.08 p = 0.68 |
| LY5+ | 15.57 ± 6.91 | 24.0 ± 4.92 p < 0.037 | — | 26.75 ± 4.11 p < 0.01 |
| | Spleen Immunophenotyping | | | |
| LY5-TCR- | 13.02 ± 2.54 | — | 16.84 ± 0.83 p < 0.0257 | — |
| CD4+ | 19.9 ± 1.09 | 22.25 ± 1.64 p ≤ 0.013 | — | 22 ± 0.47 p < 0.091 |

TABLE 13

Effect of MCT on blood and spleen immunophenotyping in cyclophosphamide (CY, 200 mg/kg) immunosuppressed mice

| Cell subsets | CY | 6.25 μM | 12.5 μM | 50 μM |
|---|---|---|---|---|
| | Blood Immunophenotyping | | | |
| LY5-TCR- | 36.82 ± 9.93 | — | 51.67 ± 11.10 p ≤ 0.05 | 46.32 ± 5.63 p = 0.1254 |
| CD11+ | 26.41 ± 4.54 | — | 42.12 ± 8.77 p < 0.0119 | 42.56 ± 8.62 p < 0.0098 |

TABLE 13-continued

Effect of MCT on blood and spleen immunophenotyping in cyclophosphamide (CY, 200 mg/kg) immunosuppressed mice

| Cell subsets | CY | 6.25 μM | 12.5 μM | 50 μM |
|---|---|---|---|---|
| Spleen Immunophenotyping | | | | |
| LY5–TCR– | 20.2 ± 4.05 | 23.92 ± 1.61 p < 0.07 (weak) | — | — |
| CD11+ | 16.31 ± 4.85 | 27.47 ± 11.48 p ≦ 0.06 (weak) | — | — |

Example 27

Chemoprotection Studies: Immunophenotyping Assay

Immunophenotyping of trimyristin, trilaurin, capric acid and sodium caproate was undertaken following the protocol described in example 26.

Table 14 represents the effect of these MCT analogues on blood and spleen immunophenotyping. On blood, trimyristin and trilaurin have no significant effect compared to cyclophosphamide alone. However on spleen, trimyristin and trilaurin enhance the relative percentage of CD11+. Furthermore, trilaurin induces a significant increase in the LY5-TCR- and NK+ cell subsets.

Interestingly, capric acid and sodium caproate significantly increase the relative percentage of LY5-TCR- on blood. On spleen, capric acid has no significant effect compared to cyclophosphamide alone.

TABLE 14

Effect of trimyristin, trilaurin, capric acid and sodium caproate on blood and spleen immunophenotyping in cyclophosphamide (CY, 200 mg/kg) immunosuppressed mice

| Compounds | Cell subsets | CY | 6.25 μM | 12.5 μM |
|---|---|---|---|---|
| Blood Immunophenotyping | | | | |
| Trimyristin | | No significant effect | | |
| Trilaurin | | No significant effect | | |
| Capric acid | LY5–TCR– | 56.36 ± 7.26 | 61.52 ± 5.16 p = 0.189 | 70.79 ± 3.95 p < 0.0029 |
| Sodium caproate | LY5–TCR– | 40.91 ± 8.84 | 52.43 ± 10.16 p = 0.063 (weak) | — |
| Spleen Immunophenotyping | | | | |
| Trimyristin | CD11+ | 16.31 ± 4.85 | 42.94 ± 8.45 p ≦ 0.0002 | — |
| Trilaurin | CD11+ | 16.31 ± 4.85 | 43.94 ± 4.78 p < 0.0001 | — |
| | LY5–TCR– | 73.17 ± 1.41 | 77.86 ± 2.94 p < 0.0097 | — |
| | NK+ | 7.53 ± 2.52 | 17.46 ± 5.80 p < 0.0067 | — |
| Capric acid | | No significant effect | | |
| Sodium caproate | | Not performed | | |

Example 28

Chemoproteetion Studies: Bone Marrow Immunophenotyping

The effect of MCT, sodium caprylate, sodium caprate on bone marrow immunophenotyping was assessed by the protocol described in example 26. Treatment with cyclophosphamide induces a significant increase in all studied subsets (CD34+, CD13+, CD41+ and CD38+). Addition of MCT or sodium caprylate or sodium caprate amplifies the number of CD13+ lineage which are myelomonocytic stem cells, myelocytes and promonocytes. This increase in the relative percentage of CD13+ is significant compared to cyclophosphamide alone. The results clearly demonstrate that MCT and other related compounds induce a significant increase in the number of bone marrow cells (as exemplified in the previous examples) and further enhance the relative percentage of precursor of phagocytic cells (PMN and monocytes). This may result in a better recovery from cytotoxic treatment or protection against infectious agents (table 15).

TABLE 15

Effect of MCT, sodium caprylate and sodium caprate on bone marrow immunophenotyping in cyclophosphamide (CY, 200 mg/kg) immunosuppressed mice

| % Cells | CD34+ | CD13+ | CD41+ | CD38+ |
|---|---|---|---|---|
| Control | 1.1 ± 0.3 | 0.8 ± 0.2 | 1.6 ± 0.2 | 29.8 ± 6.5 |
| Cyclophosphamide (CY) | 10 ± 1.0 | 3.2 ± 0.5 | 4.2 ± 0.6 | 39.6 ± 13.6 |
| CY + MCT | 11.2 ± 1.3 | 4.5 ± 0.5 p < 0.001 | 4.5 ± 0.4 | 42 ± 15.7 |
| CY + Sodium caprylate | 11.2 ± 1.3 | 4.9 ± 1.2 p < 0.017 | 4.6 ± 1.3 | 36 ± 9.7 |
| CY + Sodium caprate | 9.1 ± 3.1 | 4.7 ± 1.7 p < 0.06 | 3.7 ± 0.7 | 44.3 ± 22.8 |

Example 29

Chemoprotection Studies

The effect of tridecanoyl serinol and didecanoyl serinol on in vivo induction of immune cell proliferation or protection was assessed by the protocol described in example 16.

As shown in table 16, tridecanoyl serinol significantly enhances the spleen cell counts. No significant effect was demonstrated on bone marrow cell counts.

TABLE 16

Effect of cyclophosphamide (CY), CY + tridecanoyl serinol and CY + didecanoyl serinol on bone marrow and spleen cells

| | Bone Marrow | | | Spleen | | |
|---|---|---|---|---|---|---|
| | # Cells (×10⁶) | P/Control | P/CY | # Cells (×10⁶) | P/Control | P/CY |
| Control | 53 ± 4.8 | | | 113 ± 15.5 | | |
| CY | 28 ± 3.4 | >0.0001 | | 29 ± 9.2 | >0.0001 | |
| CY + tridecanoyl serinol | 28 ± 4.6 | >0.0001 | 0.95 | 42 ± 8.4 | >0.0001 | 0.035 |
| CY + didecanoyl serinol | 30 ± 3.8 | >0.0001 | 0.54 | 36 ± 9.9 | >0.0001 | 0.27 |

Example 30

Chemoprotection Studies

The effect of α-methyl tridecanoyl-L-fucopyranose and β-methyl tridecanoyl-L-fucopyranose on in vivo induction of immune cell proliferation or protection was assessed by the protocol described in example 16.

As shown in table 17, β-methyl tridecanoyl-L-fucopyranose demonstrated weak (not significant) activity on bone marrow cell counts compared to cyclophosphamide treated mice. The lack of activity of the α-methyl anomer is expected in view of the known instability of α-alkyl pyranosides.

TABLE 17

Effect of cyclophosphamide (CY), CY + α-methyl tridecanoyl-L-fucopyranose and CY + β-methyl tridecanoyl-L-fucopyranose on bone marrow

| | Bone Marrow | | |
|---|---|---|---|
| | # Cells ($\times 10^6$) | P/Control | P/CY |
| Control | 53 ± 8.0 | | |
| CY | 26.2 ± 2.6 | 0.0058 | |
| CY + α-methyl tridecanoyl-L-fucopyranose | 30.4 ± 9.3 | 0.0133 | 0.334 |
| CY + β-methyl tridecanoyl-L-fucopyranose | 34.6 ± 8.5 | 0.0068 | 0.061 |

Example 31

Chemoprotection Studies

The effect of ethyl caprate and capric acid N,N-dimethylacetamide ester on in vivo induction of immune cell proliferation or protection was assessed by the protocol described in example 16.

As shown in table 18, only capric acid N,N-dimethylacetamide significantly enhances the bone marrow cell count. No significant effect was demonstrated on spleen cell counts.

TABLE 18

Effect of cyclophosphamide (CY), CY + ethyl caprate and CY + capric acid N,N-dimethylacetamide on bone marrow

| | Bone Marrow | | |
|---|---|---|---|
| | # Cells ($\times 10^6$) | P/Control | P/CY |
| Control | 50.2 ± 4.8 | | |
| CY | 27.5 ± 8.0 | 0.0031 | |
| CY + ethyl caprate | 27.5 ± 4.4 | 0.0032 | 1.0 |
| CY + capric acid N,N-dimethyl-acetamide | 37.4 ± 5.9 | 0.042 | 0.036 |

Example 32

Antitumor Activity

Female 6-8-week old C57BL/6 mice were injected intravenously on day 0 with $1\times10^5$ B16F10 melanoma cells from ATCC (source of cell culture, Dr. I. J. Fidler). Animals were then injected i.v. with or without MCT (25 μMole/mouse) on day 7, 9, 14 and 16 and 10 mg/kg Doxorubicin on day 10 and 17. Mice were sacrificed on day 22. Body weight and tumor volume were recorded. Serial tumor volume was obtained by bi-dimensional diameter measurements with calipers, using the formula 0.4 ($a\times b^2$) where "a" was the major tumor diameter and "b" the minor perpendicular diameter.

This experiment was conducted to verify if MCT is not exacerbating or protecting the cancer cells rather than immune cells.

Figure 10:
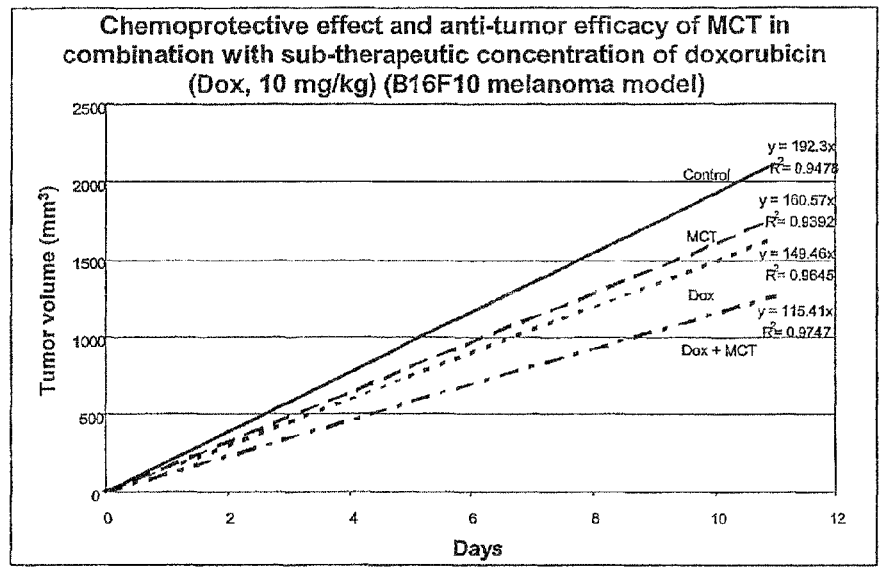
FIG. 10 represents the chemoprotective effect and anti-tumor efficacy of MCT in combination with a sub-therapeutic concentration of doxorubicin in B16F10 melanoma model.

FIG. 10 represents the chemoprotective effect and anti-tumor efficacy of MCT in combination with a sub-therapeutic concentration of doxorubicin in B16F10 melanoma model. MCT induces a weak reduction (T/C around 20%) of the tumor volume as close as the sub-therapeutic concentration of doxorubicin (TIC around 25% reduction) when used alone. An additive effect is observed when MCT is used in combination with doxorubicin (T/C around 45 to 50%). These results indicate that it is possible to attain therapeutic activity when MCT is combined with a sub-therapeutic concentration of cytotoxic drugs.

Example 33

Antitumor Activity

The syngeneic tumor DMBA3 (DA-3, breast carcinoma model) arose from a preneoplastic lesion treated with 7,12-dimethylbenzanthracene in female BALB/c mice. DA-3 cells were grown as monolayer cultures in plastic flasks in RPMI-1640 containing 0.1 mM nonessential amino acids, 0.1 μM sodium pyruvate, 2 mM L-glutamine and 100 μg/ml gentamycin sulfate. This was further supplemented with 50 μM 2-mercaptoethanol and 10% fetal bovine serum. The DA-3 tumors were serially passage in vivo by s.c. inoculation of $5\times10^5$ viable tumor cells to produce localized tumors in 6- to 8-week old BALB/c mice. The animals were then serially monitored by manual palpation for evidence of tumor. Serial tumor volume was obtained by bi-dimensional diameter measurements with calipers, using the formula OA ($a\times b^2$) where "a" was the major tumor diameter and "b" the minor perpendicular diameter. Tumors were palpable, in general, 7-10 days post-inoculation.

Two treatment regimens were used for anti-tumor efficacy and protection evaluation of MCT in combination with cyclophosphamide (CY, 100 mg/kg) and taxotere (TX, 20 mg/kg) in the DA-3 tumor model. BABL/c mice were injected with tumor cells on day 0. Treatment with MCT was done per os on day 6, 7 and 8; day 13, 14 and 15; day 20, 21 and 23 followed by treatment with CY or TX administered i.v. as single bolus injection on day 9 and 16. Body weights and tumor volumes were monitored from day 4 until day 23. At day 23, all animals were sacrificed. The % T/C (treatment over control) was calculated as the ratio of tumor volumes at termination date in the treatment group divided by the respective volumes in the control group multiplied by 100. By the NCI criteria the product is considered effective if % T/C is ≦40%.

Figure 11:
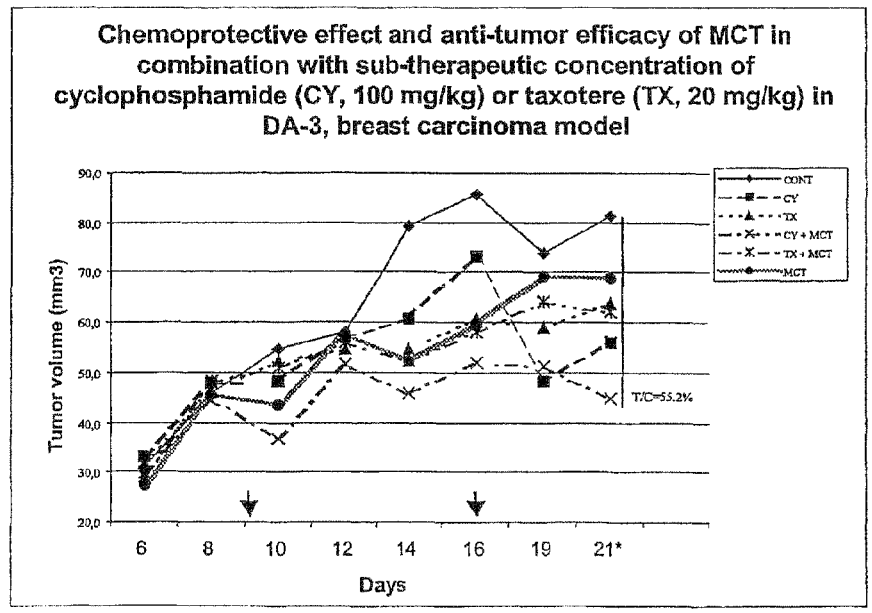
FIG. 11 represents the chemoprotective effect and anti-tumor efficacy of MCT in combination with a sub-therapeutic concentration of cyclophosphamide or taxotere in DA-3 breast carcinoma model.

This experiment was performed to verify if MCT is not exacerbating or protecting the cancer cells rather than immune cells. FIG. 11 shows the chemoprotective effect and anti-tumor efficacy of MCT in combination with sub-therapeutic concentration of CY and TX in DA-3 breast carcinoma model. MCT induces a weak reduction (T/C around 18%) of the tumor volume compared to the control. When MCT is used in combination with CY or TX, no exacerbation of the tumor volume is observed. However, when used in combination with CY, a therapeutic response is observed (T/C=39.4%). These results indicate that therapeutic activity may be attained when MCT is combined with a sub-therapeutic concentration of CY. This effect may be due to an overall increase in immune cell efficiency in MCT-treated animals (FIG. 11 and table 19).

TABLE 19

Effect of MCT on tumor volume in combination with a sub-therapeutic concentration of cyclophosphamide (CY, 100 mg/kg) and taxotere (TX, 20 mg/kg)

| | Tumor volume | Treated/Control (%) |
|---|---|---|
| Control | 58.8 ± 60.1 | |
| CY | 27.5 ± 15.9 | 46.8 |
| TX | 37.9 ± 41.5 | 64.5 |
| CY + MCT | 23.2 ± 13.1 | 39.4 |
| TX + MCT | 38.8 ± 31.0 | 66.1 |
| MCT | 48.5 ± 35.2 | 82.5 |

Example 34

Antitumor Activity

Antitumor and chemoprotection efficacy were assessed by the protocol described in example 30, with the exception of use of a therapeutic concentration of cytotoxic drugs (cyclophosphamide, 200 mg/kg; taxotere, 30 mg/kg).

Figure 12:
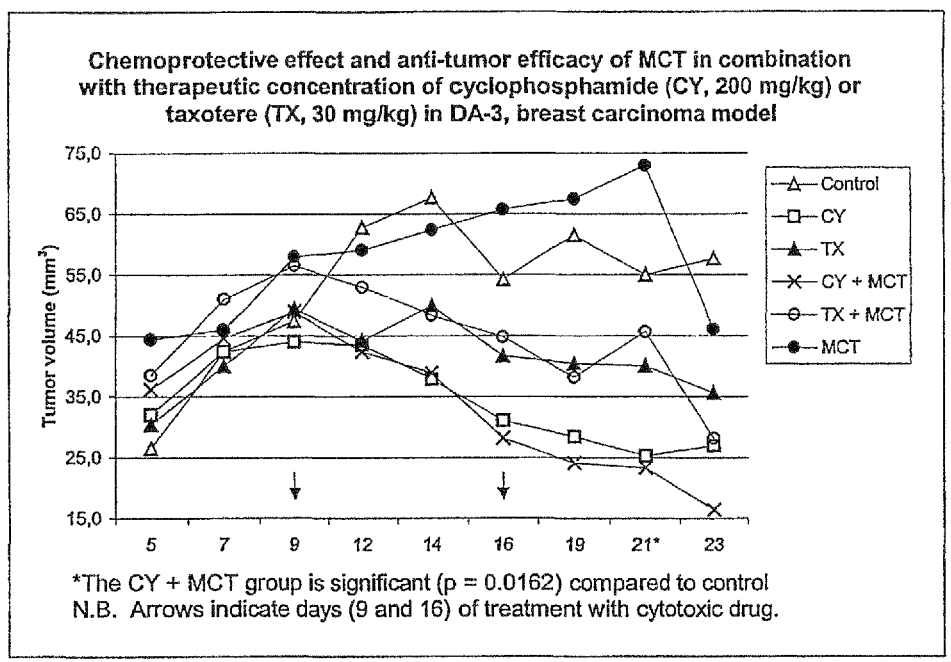
FIG. 12 shows the chemoprotective effect and anti-tumor efficacy of MCT in combination with a therapeutic concentration of cyclophosphamide or taxotere in DA-3 breast carcinoma model.

This experiment was conducted to verify if MCT is not exacerbating or protecting the cancer cells rather than immune cells. FIG. 12 shows the chemoprotective effect and anti-tumor efficacy of MCT in combination with therapeutic concentration of CY and TX in DA-3 breast carcinoma model. MCT induces a weak reduction of the tumor volume compared to the control. When MCT is used in combination with CY or TX, no exacerbation of the tumor volume is observed. When treated with CY or CY+MCT, a significant reduction of the tumor volume is observed. Furthermore, a significant response in reduction of tumor volume is attained with the treatment of MCT combined to TX (p<0.0327) compared to TX alone which is not significant compared to the control mice (p=0.1211) (table 20). These results indicate that a therapeutic activity may be attained when MCT is combined with a non-significant therapeutic concentration of TX. This effect may be due to an overall increase in immune cell efficiency in MCT-treated animals.

TABLE 20

Effect of MCT on tumor volume in combination with a therapeutic concentration of cyclophosphamide (CY, 200 mg/kg) and taxotere (TX, 30 mg/kg)

| Treatment | T/C (%) | P/Control | P/CY | P/TX |
|---|---|---|---|---|
| Control | | | | |
| MCT | | 0.4299 | | |
| CY | 18.8 | 0.0337 | | |
| CY – MCT | 22.1 | 0.0022 | 0.2928 | |
| TX | 64.7 | 0.1211 | | |
| TX – MCT | 46.7 | 0.0327 | | 0.5468 |

All references cited in this document are hereby incorporated by reference herein in their entireties.

Modifications and variations of the compositions and methods described herein will be obvious to those skilled in the art from the foregoing description. Such modifications and variations are intended to come within the scope of the appended claims.

We claim:

1. A method of stimulating hematopoiesis in a patient in need of such stimulation, said method comprising administering to the patient a pharmacologically effective amount of a composition comprising one or more compounds described by formula I

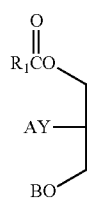

wherein
Y=O or NH;
$R_1$ is a $C_7$ or $C_9$ alkyl; and
A and B are independently hydrogen or $R_1C(O)$; and
wherein said patient undergoes bone marrow transplantation or has a condition selected from neutropenia or myelosuppression arising from chemotherapy or radiotherapy.

2. The method, according to claim 1, wherein the condition is myelosuppression arising from chemotherapy.

3. The method, according to claim 1, wherein the condition is myelosuppression arising from radiotherapy.

4. The method, according to claim 1, wherein the condition is chronic neutropenia.

5. The method, according to claim 1, wherein the condition is transient neutropenia.

6. The method, according to claim 1, wherein the condition is neutropenia arising from a hematologic disease.

7. The method, according to claim 1, wherein the condition is drug-induced neutropenia.

8. The method, according to claim 1, wherein the condition is neutropenia arising from a nutritional deficiency.

9. The method, according to claim 1, wherein the condition is neutropenia arising from infection.

10. The method, according to claim 1, wherein the condition is neutropenia arising from radiotherapy.

11. The method, according to claim 1, for the treatment of a patient undergoing bone marrow transplantation.

12. The method, according to claim 1, wherein the compound of formula I is caprylic acid triglyceride.

13. The method, according to claim 1, wherein the compound of formula I is capric acid triglyceride.

14. The method, according to claim 1, which comprises administering to the patient a mixture of two compounds, wherein A and B are $R_1C(O)$ and $R_1$ is $C_7$ and $C_9$ alkyl, respectively.

15. The method, according to claim 14, wherein $R_1$ is $CH_3(CH_2)_6$— and $CH_3(CH_2)_8$—, respectively.

16. The method, according to claim 1, which comprises administering four geometric isomers of $C_8$ and $C_{10}$ fatty acid triglycerides described by the following formula:

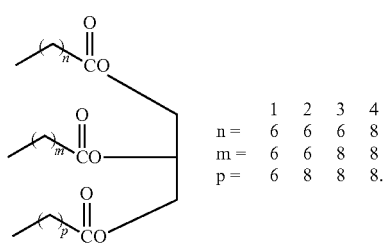

|   | 1 | 2 | 3 | 4 |
|---|---|---|---|---|
| n = | 6 | 6 | 6 | 8 |
| m = | 6 | 6 | 8 | 8 |
| p = | 6 | 8 | 8 | 8. |

17. The method, according to claim 1, wherein the patient is undergoing separate or simultaneous administration of a human colony-stimulating factor.

18. The method, according to claim 17, wherein the colony-stimulating factor is Granulocyte colony-stimulating factor (G-CSF) or Granulocyte macrophage colony-stimulating factor (GM-CSF).

19. The method, according to claim 1, wherein the patient is undergoing simultaneous administration of a human cytokine.

20. The method, according to claim 19, wherein the cytokine is interleukin 2 or interleukin 15.

* * * * *